(12) United States Patent
Friedman et al.

(10) Patent No.: US 7,135,034 B2
(45) Date of Patent: Nov. 14, 2006

(54) FLEXIBLE ARRAY

(75) Inventors: Marc D. Friedman, Needham, MA (US); Stephen Evans, Westford, MA (US); Paul J. Zalesky, Cranston, RI (US); Jon Dahm, Boulder, CO (US); Philip Levin, Storrs, CT (US)

(73) Assignee: LumeRx, Inc., Marlborough, MA (US)

( * ) Notice: Subject to any disclaimer, the term of this patent is extended or adjusted under 35 U.S.C. 154(b) by 157 days.

(21) Appl. No.: 10/878,648

(22) Filed: Jun. 28, 2004

(65) Prior Publication Data

US 2005/0104059 A1 May 19, 2005

Related U.S. Application Data

(60) Provisional application No. 60/520,465, filed on Nov. 14, 2003.

(51) Int. Cl.
*A61N 5/06* (2006.01)
*F21V 33/00* (2006.01)

(52) U.S. Cl. .............. 607/88; 606/9; 362/555
(58) Field of Classification Search ........ 362/551–555; 606/1–2; 607/88–93
See application file for complete search history.

(56) References Cited

U.S. PATENT DOCUMENTS

| | | | |
|---|---|---|---|
| 4,195,637 A | 4/1980 | Gruntzig et al. | |
| 4,998,930 A | 3/1991 | Lundahl | |
| 5,125,925 A | 6/1992 | Lundahl | |
| 5,165,773 A | 11/1992 | Nath | |
| 5,342,301 A | 8/1994 | Saab | |
| 5,342,305 A | 8/1994 | Shonk | |
| 5,344,419 A | 9/1994 | Spears | |
| 5,354,293 A | 10/1994 | Beyer et al. | |
| 5,415,654 A | 5/1995 | Daikuzono | |
| 5,440,461 A * | 8/1995 | Nadel et al. | ................ 362/103 |
| 5,445,608 A | 8/1995 | Chen et al. | |
| 5,452,182 A | 9/1995 | Eichelberger et al. | |
| 5,458,575 A | 10/1995 | Wang | |
| 5,514,091 A | 5/1996 | Yoon | |
| 5,514,669 A | 5/1996 | Selman | |
| 5,519,596 A * | 5/1996 | Woolverton | ................ 362/250 |
| 5,558,668 A | 9/1996 | Lankford et al. | |
| 5,607,419 A | 3/1997 | Amplatz et al. | |
| 5,720,717 A | 2/1998 | D'Andrea | |
| 5,766,234 A | 6/1998 | Chen et al. | |
| 5,788,708 A | 8/1998 | Hegde et al. | |
| 5,800,478 A | 9/1998 | Chen et al. | |
| 5,814,039 A | 9/1998 | Prescott | |
| 5,861,020 A | 1/1999 | Schwarzmaier | |
| 5,876,426 A | 3/1999 | Kume et al. | |

(Continued)

FOREIGN PATENT DOCUMENTS

EP 0 311 458 4/1989

(Continued)

*Primary Examiner*—Henry M Johnson, III
(74) *Attorney, Agent, or Firm*—Dana M. Gordon; Foley Hoag LLP

(57) ABSTRACT

Physically flexible radiation-emitting probes and associated illumination methods and systems for delivering radiation or light to the interior of a lumen or cavity. Light-emitting devices are immersed in a flowing liquid coolant within a probe to provide high light output power, and convoluted electrical power buss structures provide physical flexibility of a probe about a longitudinal axis. The probes can be configured for delivering light to the interior of any lumen including for performing therapeutic medical procedures at locations in body lumens including the interior of the human gastrointestinal tract.

26 Claims, 19 Drawing Sheets

U.S. PATENT DOCUMENTS

| | | | |
|---|---|---|---|
| 5,876,427 A | 3/1999 | Chen et al. | |
| 5,947,924 A | 9/1999 | Liprie | |
| 5,957,960 A | 9/1999 | Chen et al. | |
| 5,997,569 A | 12/1999 | Chen et al. | |
| 5,997,571 A | 12/1999 | Farr et al. | |
| 6,013,053 A | 1/2000 | Bower et al. | |
| 6,086,558 A | 7/2000 | Bower et al. | |
| 6,146,409 A | 11/2000 | Overholt et al. | |
| 6,159,236 A | 12/2000 | Biel | |
| 6,187,014 B1 | 2/2001 | Goodin et al. | |
| 6,224,590 B1 | 5/2001 | Daikuzono | |
| 6,254,570 B1 | 7/2001 | Rutner et al. | |
| 6,267,717 B1 | 7/2001 | Stoll et al. | |
| 6,290,713 B1 | 9/2001 | Russell | |
| 6,364,874 B1 | 4/2002 | Bays et al. | |
| 6,371,637 B1 | 4/2002 | Atchinson et al. | |
| 6,443,978 B1 | 9/2002 | Zharov | |
| 6,480,389 B1 | 11/2002 | Shie et al. | |
| 6,491,618 B1 | 12/2002 | Ganz | |
| 6,491,662 B1 | 12/2002 | Liprie et al. | |
| 6,491,672 B1 | 12/2002 | Slepian et al. | |
| 6,514,192 B1 | 2/2003 | Tiren | |
| 6,566,824 B1 * | 5/2003 | Panagotacos et al. | 315/291 |
| 6,580,228 B1 * | 6/2003 | Chen et al. | 315/185 R |
| 6,605,084 B1 | 8/2003 | Acker et al. | |
| 6,610,083 B1 | 8/2003 | Keller et al. | |
| 6,626,900 B1 | 9/2003 | Sinofsky et al. | 606/15 |
| 6,645,230 B1 | 11/2003 | Whitehurst | |
| 6,682,525 B1 | 1/2004 | Lalonde et al. | |
| 6,699,170 B1 | 3/2004 | Crocker et al. | |
| 6,702,782 B1 | 3/2004 | Miller et al. | |
| 6,706,004 B1 | 3/2004 | Tearney et al. | |
| 6,706,010 B1 | 3/2004 | Miki et al. | |
| 6,712,833 B1 | 3/2004 | Lee et al. | |
| 6,719,720 B1 | 4/2004 | Voelker et al. | |
| 6,723,053 B1 | 4/2004 | Ackerman et al. | |
| 6,723,070 B1 | 4/2004 | Arai et al. | |
| 6,723,113 B1 | 4/2004 | Shkolnik | |
| 6,732,734 B1 | 5/2004 | Ogushi et al. | |
| 6,733,487 B1 | 5/2004 | Keith et al. | |
| 6,733,512 B1 | 5/2004 | McGhan | |
| 6,736,808 B1 | 5/2004 | Motamedi et al. | |
| 6,736,827 B1 | 5/2004 | McAndrew et al. | |
| 6,740,104 B1 | 5/2004 | Solar et al. | |
| 6,743,227 B1 | 6/2004 | Seraj et al. | |
| 6,746,423 B1 | 6/2004 | Wantink | |
| 6,746,424 B1 | 6/2004 | Stamberg | |
| 6,749,583 B1 | 6/2004 | Briscoe et al. | |
| 6,749,623 B1 | 6/2004 | Hsi et al. | |
| 6,815,724 B1 | 11/2004 | Dry | |
| 6,831,303 B1 | 12/2004 | Dry | |
| 2001/0049464 A1 | 12/2001 | Ganz | |
| 2001/0053920 A1 | 12/2001 | Shaker | |
| 2002/0010500 A1 | 1/2002 | Chen | |
| 2002/0055748 A1 | 5/2002 | Gellman et al. | |
| 2002/0135665 A1 | 9/2002 | Gardner | |
| 2002/0165521 A1 | 11/2002 | Cioanta et al. | |
| 2002/0183620 A1 | 12/2002 | Tearney et al. | |
| 2003/0028182 A1 | 2/2003 | Abboud et al. | |
| 2003/0032950 A1 | 2/2003 | Altshuler et al. | |
| 2003/0090893 A1 | 5/2003 | Nepil | |
| 2003/0123225 A1 | 7/2003 | Miller | |
| 2003/0191459 A1 | 10/2003 | Ganz et al. | |
| 2003/0201542 A1 | 10/2003 | Wu | |
| 2004/0037080 A1 | 2/2004 | Luk et al. | |
| 2004/0039242 A1 | 2/2004 | Tolkoff et al. | |
| 2004/0059397 A1 | 3/2004 | Sinofsky et al. | 607/88 |
| 2004/0093044 A1 | 5/2004 | Rychnovsky et al. | |
| 2004/0223328 A1 | 11/2004 | Lee et al. | |
| 2004/0225322 A1 | 11/2004 | Garrison et al. | |
| 2005/0030765 A1 * | 2/2005 | Southard et al. | 362/559 |

FOREIGN PATENT DOCUMENTS

| | | |
|---|---|---|
| JP | 10-094583 | 4/1998 |
| WO | WO 02/07629 | 1/2002 |
| WO | WO 2005/004704 A2 | 1/2005 |

* cited by examiner

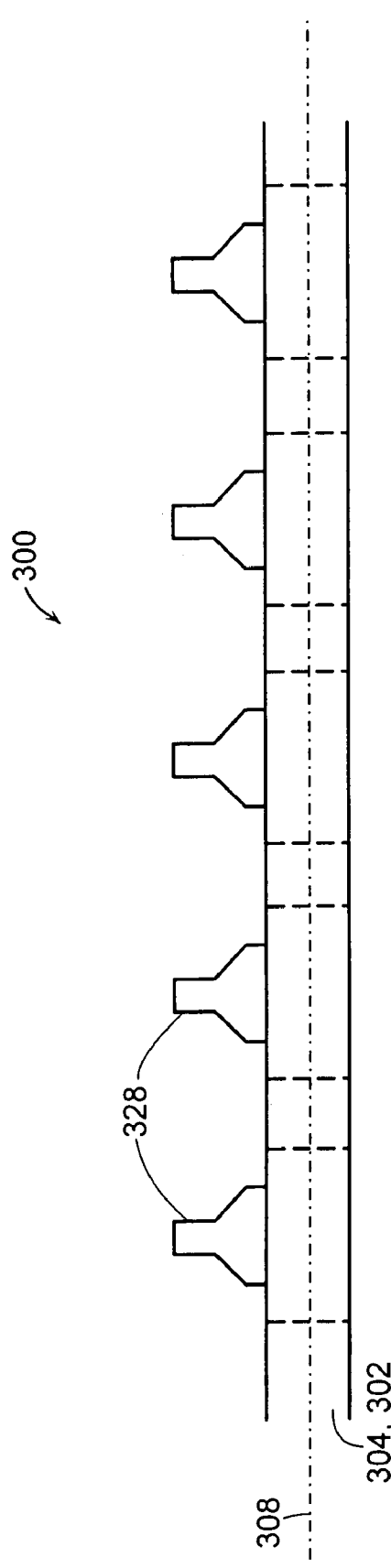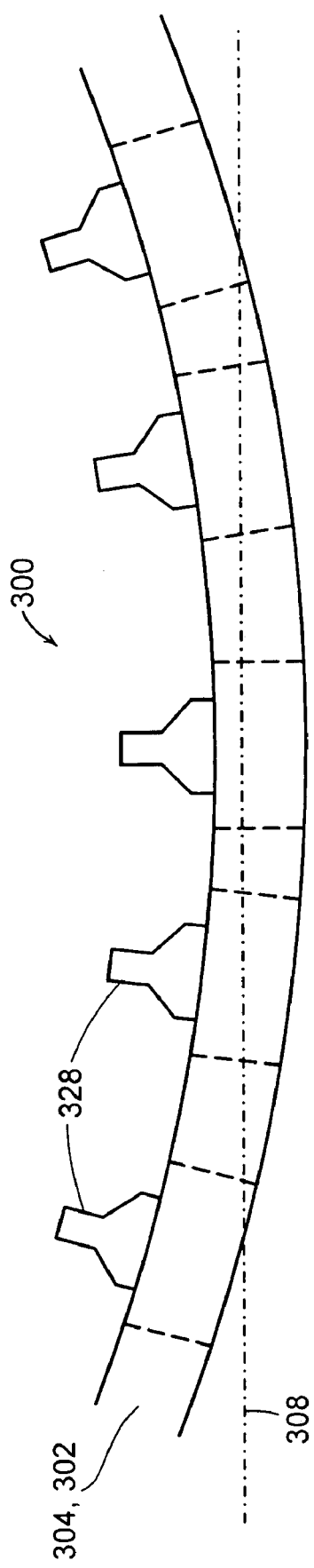

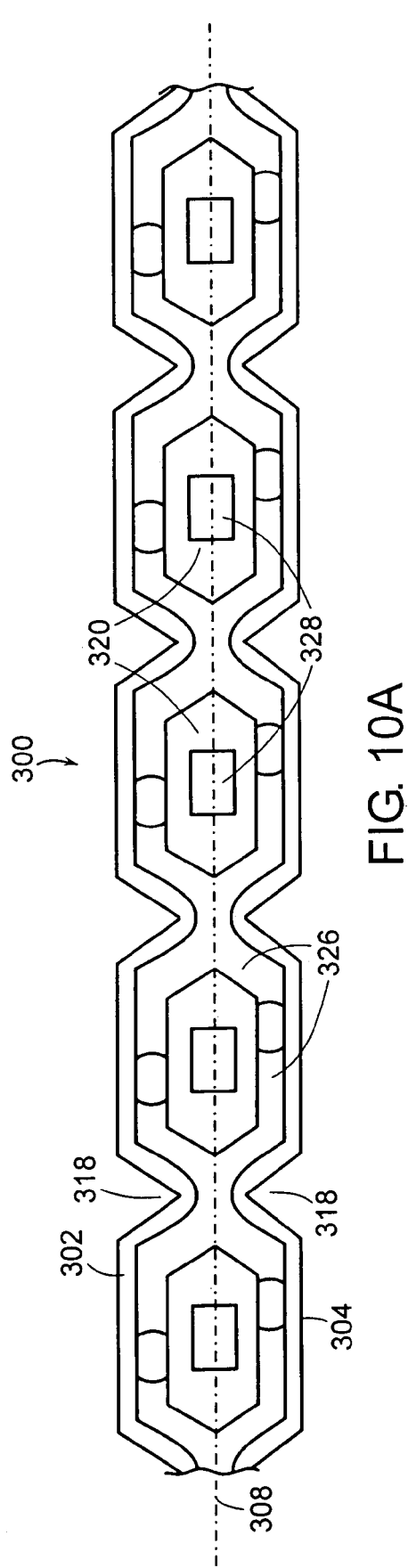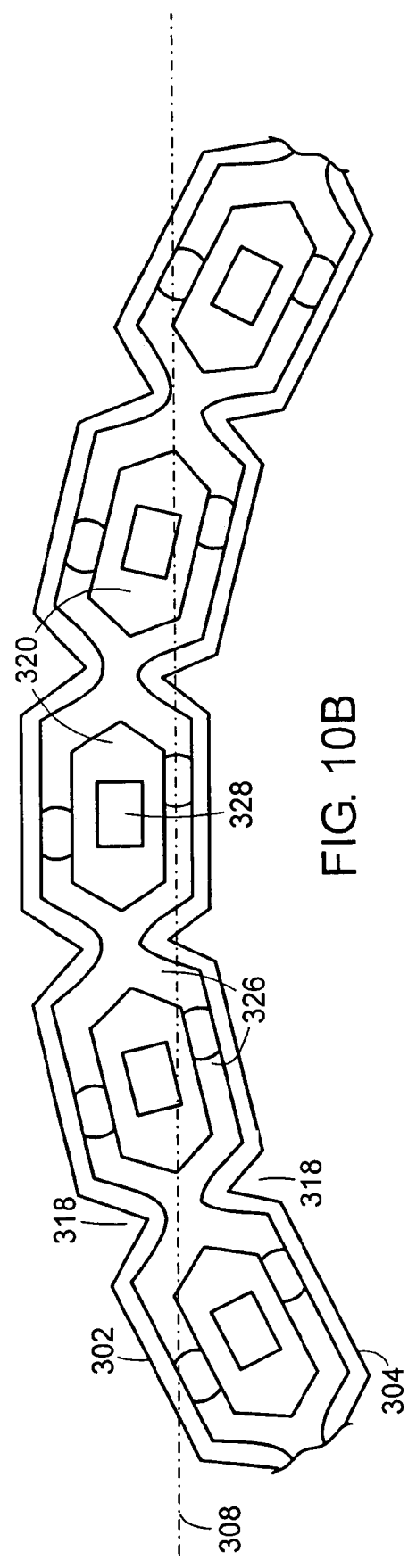
FIG. 10A
FIG. 10B

FLEXIBLE ARRAY

RELATED APPLICATIONS

This application incorporates by reference, and claims priority to and the benefit of U.S. Provisional Application No. 60/520,465, filed on Nov. 14, 2003. The present application related to co-pending application Ser. No. 10/878,649 filed on the same date as this application, entitled "Phototherapy Device and System", by inventors Marc D. Friedman, Stephen Evans, Paul J. Zalesky, Jon Dahm, and Philip Levin, and such co-pending application is incorporated by reference.

FIELD

This invention related to apparatus and methods for delivering radiation, including delivering radiation to a surface on or within a living body and, more particularly, to apparatus and methods for using light to debilitate or kill microorganisms on or within a body cavity of a patient.

BACKGROUND

Infections involving the human gastrointestinal tract and other body lumens are extremely common, involving many millions of people on an annual basis. These infections are responsible for significant illness, morbidity and death. One of the most common gastrointestinal infections is a chronic infection with *Helicobacter pylori* (*H. pylori*), a bacterial pathogen that infects the stomach and duodenum. In industrialized nations such as the United States, *H. pylori* may be found in 20% or more of the adult population. In some South American countries, the *H. pylori* infection rate approaches 90%. Although infection with H. pylori can be asymptomatic, in a significant minority of infected people it is associated with serious conditions including gastritis, gastric ulcer, duodenal ulcer, gastric cancer, and gastric lymphoma. *H. pylori* is believed to be responsible for approximately 90% of all reported duodenal ulcers, 50% of gastric ulcers, 85% of gastric cancer, and virtually 100% of gastric lymphoma.

The most common treatment currently available for *H. pylori* infection is a complex antibiotic regimen involving three or four expensive drugs given over a two-week period. Even with antibiotic treatment, 20% or more of those treated are not cured of their infection. Further, the powerful antibiotics used are not well tolerated by some patients, variously causing allergic reactions, nausea, an altered sense of taste and diarrhea. In addition, antibiotic resistance by this and many other pathogenic organisms is growing rapidly. Up to 50% of *H. pylori* isolates are now resistant to one or more of the best antibiotics known to cure the infection. No vaccine is yet available for *H. pylori*, despite years of intensive effort.

Therapeutic methods that do not rely solely on drugs to treat disease thus have significant potential advantages over antibiotic therapy for bacterial infections. Photodynamic therapy (PDT) is a light therapy that includes pretreatment with a photosensitizing drug, followed by illumination of the treatment area to kill cells having a high concentration of the drug, which preferentially absorbs light at specific wavelengths. A typical application of this method is to debilitate or destroy malignant tumor cells that have preferentially retained the photosensitizing drug, while preserving adjacent normal tissue. Direct deactivation or killing of *H. Pylori* and other microorganisms has been demonstrated using light, without requiring pretreatment with a photosensitizer.

Broad deployment of light therapy for *H. Pylori* and other intraluminal infections will require practical and reliable light sources with which to effect such treatment. Access can be gained to some treatment sites within the body, including interior surfaces of the digestive tract, using light sources configured as elongate probes that can be guided through an external orifice into the body and to the treatment site. One such minimally invasive approach is to deliver light to the interior of a body lumen through an optical fiber that is optically coupled to a remotely located high power laser. This approach to light therapy is expensive, generally lacks portability, and is impractical for delivering light to large intraluminal treatment areas.

An alternative approach for developing minimally invasive probes for intraluminal light therapy is to utilize electrically excited light-emitting devices such as light-emitting diodes within a probe. One problem associated with this approach is that the light-emitting devices confined within an elongated probe produce waste heat when electrically excited, thereby significantly limiting the maximum average light output power achievable from the probe without thermally damaging the light-emitting devices, and without exceeding safe temperatures for exposure of the probe to body tissue at the treatment site.

Additionally, it would be advantageous for a probe to be made physically flexible to be safely guided through narrow passages in the body and positioned at a treatment site. Attempts to address these problems may be found in U.S. Pat. Nos. 5,800,478 and 5,576,427. However, each one of these references suffers from a variety of disadvantages, including one or more of the following disadvantages: the probe is lacking flexibility in the plane of a substrate on which the array of light-emitting devices is constructed, and thermal dissipation of the probe at high light output power is not addressed.

Thus, a great need exists for new devices and systems to deliver light to an interior of a lumen, for treatment of *H. pylori* and other intraluminal infections. There also exists a need for apparatus and methods to deliver light to lumens of the body in a safe and effective manner. In addition, generally there exists a need for the effective delivery of light to an interior space that may benefit from treatment with radiation including light.

SUMMARY

The present invention relates to delivering radiation or light to an interior of an object or an organism to effect or facilitate a chemical or biological reaction, including devices and methods for delivering light to the interior of a lumen, to effect a treatment at a wall of the lumen. The invention is particularly useful for performing therapeutic medical procedures on the interior of a lumen, for example, the gastrointestinal tract of a living human or animal. The invention can also be applied to deliver light to the interior surface of any structure into which the apparatus can be disposed. The invention also relates to systems for the diagnosis and treatment of infections within a lumen in a patient.

One aspect of the present invention is a flexible array. The array includes a first flexible conductive buss and a second flexible conductive buss, each of which has a respective longitudinal axis. The first buss and the second buss are substantially parallel and not directly in contact with each other. The array also includes a plurality of platforms disposed between the first buss and the second buss, each of the plurality of platforms being connected to the first buss by a first member and to the second buss by a second member. The array further includes at least one radiation-emitting device disposed on at least one of the plurality of platforms, and electrically coupled to the first buss and the second buss by at least one flexible electrical lead. In one embodiment, the at least one radiation-emitting device is a light-emitting diode.

In an embodiment, the first member is flexible and the second member is flexible, the first buss has a first buss side surface and the second buss has a second buss side surface, and each of the plurality of platforms has a first platform side surface and a second platform side surface. In this embodiment, each first member is disposed between the first buss side surface and a first platform side surface, and each second member is disposed between the second buss side surface and a second platform side surface.

In another embodiment, the first member is flexible and the second member is flexible, the first buss has a first top surface and the second buss has a second top surface, and each of the platforms has a top surface and a bottom surface, and each first member is disposed between the first top surface and a bottom surface, and each second member is disposed between the second top surface and a bottom surface. In any of the above embodiments, either or both of the first and the second buss may be in the same plane and may include one or more convolutions along its respective longitudinal axis.

In yet another embodiment, the at least one radiation-emitting device is a light-emitting diode. In other embodiments, the at least one radiation-emitting device emits radiation substantially within a band of wavelengths adapted to treat diseased tissue, or substantially within a band of wavelengths adapted to modify the rate of a chemical reaction. In an embodiment, the band of wavelengths is substantially centered between approximately 400 nanometers and 410 nanometers. In another embodiment, the at least one radiation-emitting device emits radiation.

Radiation-emitting devices may be arranged in a variety of physical configurations in an array of the present invention. In one embodiment, the at least one radiation-emitting devices includes at least two radiation-emitting devices. In another embodiment, one of the at least two radiation-emitting devices is disposed on a top surface and the other is disposed on a bottom surface. In yet another embodiment, the at least one radiation-emitting devices is a plurality of radiation-emitting devices, and the at least one flexible electrical leads comprises a plurality of electrical leads. In still another embodiment, the plurality of flexible electrical leads electrically couple the plurality of radiation-emitting devices between the first buss and the second buss in a series-parallel circuit. The series-parallel circuit may include any number of radiation-emitting devices in series. In one embodiment, the series-parallel circuit comprises a plurality of groups of at least four radiation-emitting devices in series, the plurality of groups being electrically in parallel.

Another aspect of the present invention is a flexible array that includes a plurality of segments. Each of the segments has a first flexible conductive buss and a second flexible conductive buss, the first buss and the second buss being substantially parallel and not directly in contact with each other. The array also includes a plurality of platforms disposed between the first buss and the second buss, the platforms being connected to the first buss by a first member and to the second buss by a second member, either or both of which may be flexible. At least one electrical device is disposed on at least one platform, and electrically connected to the first buss and the second buss. In an embodiment, the electrical devices are light-emitting diodes. The array further includes a plurality of flexible electrical connectors. At least one of the plurality of electrical connectors is disposed between the first flexible bus of one segment and the first flexible bus of a second segment, and at least one electrical connector being disposed between the second flexible bus of one segment and the second flexible bus of a second segment.

In an embodiment, the plurality of flexible electrical connectors are adapted to position the segments within an elongated probe, the positioning being in one or more geometrical plane. In another embodiment, wherein the first buss and the second buss each have a longitudinal axis, each of the first and the second buss includes a plurality of convolutions along its respective longitudinal axis. In another embodiment, the at least one electrical device emits radiation substantially within a band of wavelengths adapted to treat diseased tissue.

Yet another aspect of the present invention is an apparatus for delivering radiation. The apparatus includes at least one longitudinal array having a first flexible conductive buss and a second flexible conductive buss, the first buss and the second buss being substantially parallel and not directly in contact with each other. The first buss and the second buss each include a plurality of convolutions. A plurality of platforms is disposed between the first buss and the second buss, the platforms being connected to the first buss by a first member and to the second buss by a second member. The apparatus also includes a plurality of radiation-emitting devices, each disposed on one of the plurality of platforms, and electrically coupled to the first buss and the second buss. The array further includes a flexible shaft having a distal end and a proximal end. The shaft includes an outer surface defining at least one groove extending from a location near the distal end to the proximal end. A flexible sheath is located proximate the shaft, the sheath and the at least one groove defining at least one channel, the at least one array disposed in the at least one channel.

The foregoing and other features and advantages of the present invention will become more apparent from the following description, accompanying drawings and claims.

BRIEF DESCRIPTION OF THE DRAWINGS

Aspects and features of the present invention may be better understood by referring to the following description in conjunction with the accompanying drawings and claims, in which like numerals indicate like structural elements and features in various figures. The drawings are not necessarily to scale, emphasis instead being placed upon illustrating embodiments and features of the invention.

FIG. 9A and FIG. 9B illustrate a side view of the light-emitting diode array of FIG. 8, and an out-of-plane flexion of the array, respectively.

FIG. 10A and FIG. 10B illustrate a plan view of the light-emitting diode array of FIG. 8, and an in-plane flexion of the array, respectively.

DESCRIPTION

Figure 1:
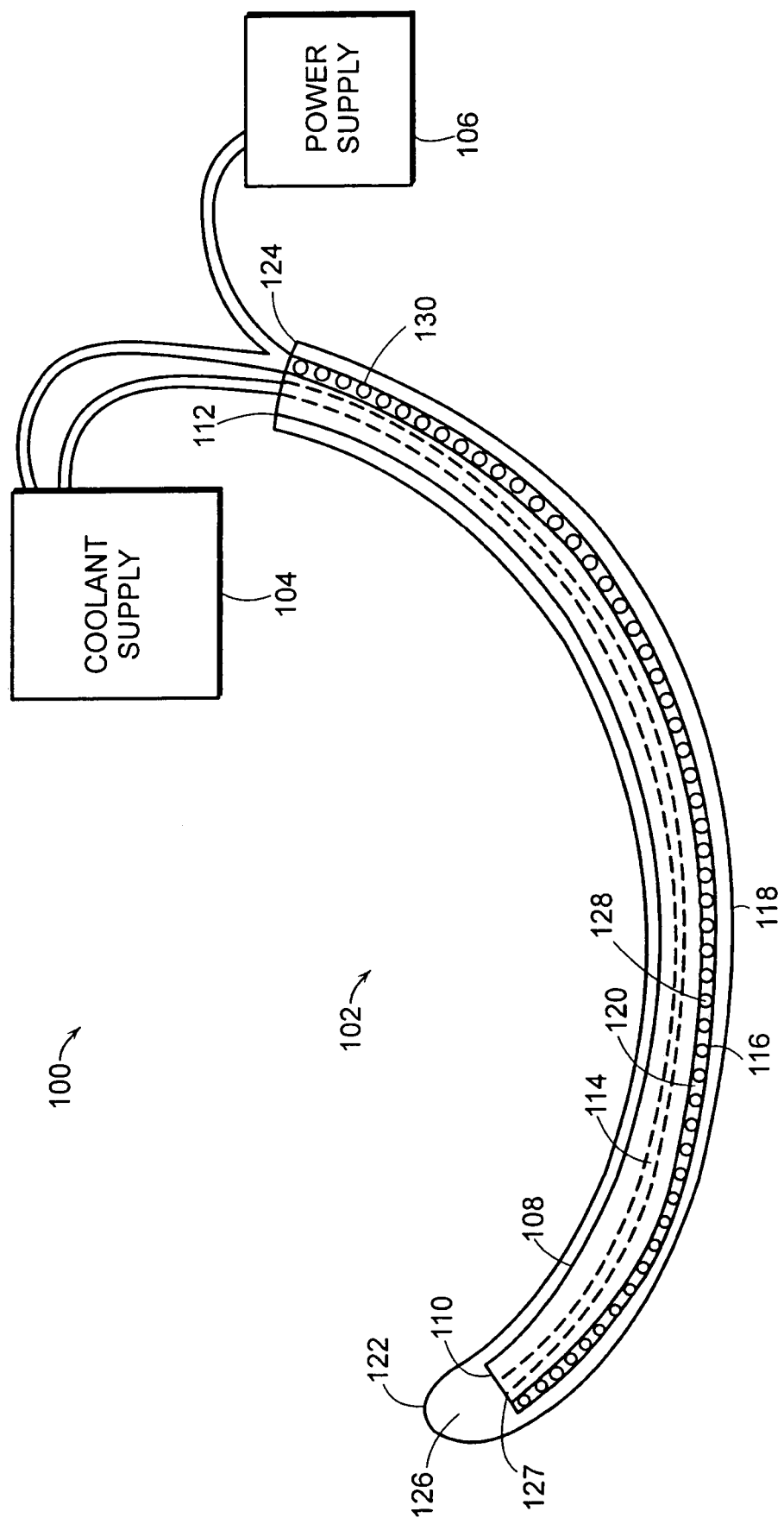
FIG. 1 is a schematic cross sectional overview of a light-emitting probe system according to the present invention.

Certain exemplary embodiments will now be described to provide an overall understanding of the aspects and features of the apparatus, systems and methods of use disclosed herein. Examples of these embodiments and features are illustrated in the drawings. Those of ordinary skill in the art will understand that the apparatus, systems and methods of use disclosed herein can be adapted and modified to provide apparatus, systems and methods for other applications and that other additions and modifications can be made without departing from the scope of the present disclosure. For example, the features illustrated or described as part of one embodiment or one drawing can be used on another embodiment or another drawing to yield yet another embodiment. Such modifications and variations are intended to be included within the scope of the present disclosure.

The present invention relates to devices, systems and methods for delivering radiation or light to an interior, including to an interior of a lumen. The term lumen is used herein to mean the interior of a hollow organ in a human or animal body, and more generally to refer to any tubular or hollow item. Among other things, the invention also relates to systems for the diagnosis and treatment of infections within a lumen in a patient.

An exemplary embodiment of a radiation-generating system or light-generating system 100 of the present invention is illustrated in FIG. 1. The light-generating system 100 includes an elongate light-emitting probe 102, a coolant supply 104 for cooling the probe, and a power supply 106 for energizing the probe. The probe 102 includes a flexible shaft 108 having a distal shaft end 110, a proximal shaft end 112 and a bore 114 extending longitudinally through the shaft 108 between the distal shaft end 110 and the proximal shaft end 112. The shaft 108 may comprise a flexible material that is electrically nonconductive. The terms electrically nonconductive and electrically insulating are used interchangeably herein.

Examples of materials appropriate for constructing the shaft 108 include natural and synthetic polymers such as polyolefins, fluoropolymers, polyurethanes, polyesters, and rubber products. For some embodiments, the material of the shaft 108 is also chosen to be optically transparent, translucent or reflective at an optical emission wavelength of the light-emitting probe. For some embodiments, the material of the shaft 108 is chosen to be compatible with selected liquid coolants discussed hereinbelow. For some embodiments, the material of the shaft 108 is chosen to be biocompatible, that is, safe for direct contact with living tissue. In an embodiment, the shaft 108 is made of Fluorinated Ethylene Propylene polymer (FEP). In another embodiment, the shaft 108 is made of polytetrafluoroethylene (Teflon). FEP and Teflon are trademarks of DuPont.

A continuous groove 116 extends longitudinally along the shaft 108 from the distal shaft end 110 substantially to the proximal shaft end 112. A sheath 118 that may be flexible and transparent closely surrounds the shaft 108, defining a continuous longitudinal channel or passage 120 within the groove 116. The sheath 118 has a distal sheath end 122 and a proximal sheath end 124. The distal sheath end 122 extends distally beyond the distal shaft end 110 and is closed, defining a plenum volume 126 between the distal sheath end 122 and the distal shaft end 110. The passage 120 is in fluid communication with the bore 114 substantially at the distal shaft end 110. Fluid communication between the passage 120 and the bore 114 may be provided by the plenum volume 126. An interior channel 127 may also be provided to provide fluid communication between the passage 120 and the bore 114. The sheath 118 preferably comprises a flexible polymeric material that is electrically nonconductive.

The sheath 118 and the shaft 108 may be fabricated or formed as a unitary part. Alternatively, instead of using a sheath, strips of any appropriate shape of material adapted to the shape, width and length of the groove 116 may be secured over the groove 116 to form a passage 120. In such case, instead of the sheath 118 defining a plenum volume, a cap or similar item may be secured at the distal shaft end 110 to define a plenum volume.

Examples of materials appropriate for constructing the sheath 118 include natural and synthetic polymers such as polyolefins, fluoropolymers, polyurethanes, polyesters, and rubber products. The material of the sheath 118, either in whole or in part, is also chosen to be optically transparent, translucent or reflective at an optical emission wavelength of the light-emitting probe. The optical properties of the sheath 118 (or the strips discussed above) may also be patterned to selectively transmit, scatter, reflect, or absorb light at an optical emission wavelength of the probe 102 as a function of position along the probe 102 or circumferentially about the probe 102. For some embodiments, the material of the shaft 108 is also chosen to be compatible with selected liquid coolants discussed hereinbelow. For some embodiments, the material of the sheath 118 is preferably chosen to be biocompatible. In an embodiment, the sheath 118 is preferably made of Fluorinated Ethylene Propylene polymer (FEP). In another embodiment, the sheath 118 is preferably made of polyethylene.

In some embodiments, one or both of the sheath 118 and the shaft 108 is impregnated with an optically scattering material, is provided with a reflective coating or includes a wavelength-converting material. The sheath may also be patterned to provide different optical properties depending on a position along the probe 102.

The passage 120 and the bore 114 together define a coolant loop within the probe 102. At substantially the proximal shaft end 112 and the proximal sheath end 124, each of the bore 114 and the passage 120 is coupled to the coolant supply 104 for flowing an electrically nonconductive liquid coolant through the loop. The coolant has optical properties suitable for passing light out of the probe and, for use in medical applications, is preferably chosen to be a room-temperature liquid that is safe for contact with living tissue (a biosafe liquid).

Examples of coolants suitable for use in a probe of the present invention include fluorinated organic compounds, silicone oils, hydrocarbon oils and deionized water. A coolant may also be selected to have a boiling temperature that is lower than a scalding temperature of living tissue. Such a fluid vaporizes before becoming hot enough to scald tissue. In an embodiment, the coolant is selected to have a boiling temperature lower than about 45 degrees Celsius. Coolants having a boiling point suitable for preventing scalding of tissue are available commercially. For example, 3M Corporation manufactures such a coolant under the trade name Fluorinert.

In an embodiment related to medical device applications, coupling between the loop and the coolant supply 104 can be any fluid coupling means appropriate for incorporation into medical apparatus. In an embodiment, coupling between the loop and the coolant source comprises quick-connect plumbing fittings. In an embodiment, the coolant supply 124 is a recirculating coolant system that maintains coolant flowing through the loop at substantially a constant temperature. In one embodiment, coolant flows distally through the bore 114 and proximally through the passage 120. In another embodiment, coolant flows distally through the passage 120 and proximally through the bore 114.

A plurality of light-emitting devices 128 is disposed within the passage 120, spaced apart as a longitudinal array. The plurality of light-emitting devices 128 is immersed in the coolant within the passage 120 and oriented to direct emitted light out of the probe 102 through the coolant and the sheath 118. The plurality of light-emitting devices 128 may also include passive or active electronic sensors, active devices such as acoustic or ultrasonic transducers, radiation-emitting devices, electrically-energized radiation sources such as x-ray sources (which are very short wavelength light sources) or combinations thereof. The light-emitting devices may be substituted in whole or in part by the foregoing electronic devices in a probe of the present invention. The sheath 118 may be opaque in particular in probes lacking optical sensors or light-emitting devices. In an embodiment, preferably all or substantially all of the sheath 118 near the plurality of light-emitting devices 128 is optically transparent, translucent or reflective at an optical emission wavelength of the light-emitting probe 102.

Each of the plurality of light-emitting devices 128 is electrically connected in a circuit that is energized through a plurality of electrical leads 130 routed through the passage 120 to the proximal shaft end 112, and coupled to the power supply 106 for energizing the plurality of light-emitting devices 128. In connection with medical applications, coupling between the plurality of electrical leads 130 and the power supply 106 can be any electrical coupling means appropriate for incorporation into a medical apparatus. In an embodiment, the electrical leads 130 are coupled to the power supply 106 by an electrically shielded in-line connector. In another embodiment, the proximal shaft end 112 and the proximal sheath end 124 are connected to an integrated assembly having both coolant and electrical connectors mounted thereon. In an embodiment, the electrical power supply 106 is a regulated power supply that regulates light output from the plurality of light-emitting devices 128. In an embodiment a signal provided by a sensor mounted within the probe 102 is used to control the power supply 106.

The effects of light incident on a biological tissue or on a non-living material can depend on the wavelength of the incident light. For example, light in the wavelength range of 360 nanometers (nm) to 650 nm, and preferably in a wavelength range of 400 nm to 410 nm, centered near 405 nm, has been demonstrated to disable or kill *H. Pylori* bacteria without substantial damage to adjacent healthy tissue. The plurality of light-emitting devices 128 can be constructed to emit light within one or more predetermined range of wavelengths (emission band) targeting absorption bands of a selected photosensitizer. For example, the plurality of light-emitting elements 128 can comprise light-emitting diodes manufactured to have an emission band centered at a selected infrared, visible or near-ultraviolet wavelength that induces a photochemical reaction in a target material. In an embodiment, the plurality of light-emitting devices 128 emits light substantially within an emission band operative to disable or kill a bacterium without substantially damaging adjacent healthy tissue.

The coolant and the sheath 118 transmit at least a portion of the light emitted by the plurality of light-emitting devices 128. The coolant may be either substantially transparent to the light or may scatter the light, in the latter case making the coolant appear translucent. We use the term transmissive herein to describe both transparent and translucent materials. Similarly, the sheath 118 may be either substantially transparent or translucent in its entirety or substantially solely in locations proximate to the light-emitting devices 128. In an embodiment, each of the coolant and the sheath 118 is substantially transparent to light emitted by the plurality of light-emitting devices. Optically transparent materials for probes of the present invention are preferably selected so as to transmit least approximately 50% and preferably greater than 80% of the light emitted by light-emitting devices in the probe and directed through the transparent materials to exit the probe.

Light-emitting surfaces of the light-emitting devices may be coated with a transparent film that grades the refractive index at the interface between the light-emitting device and the coolant, thereby reducing reflective losses at that interface. The refractive index-grading material may comprise a curable silicone adhesive. In an embodiment, the refractive index grading material is a silicone encapsulant having a refractive index in the range of about 1.45 to 1.55.

Figure 2:
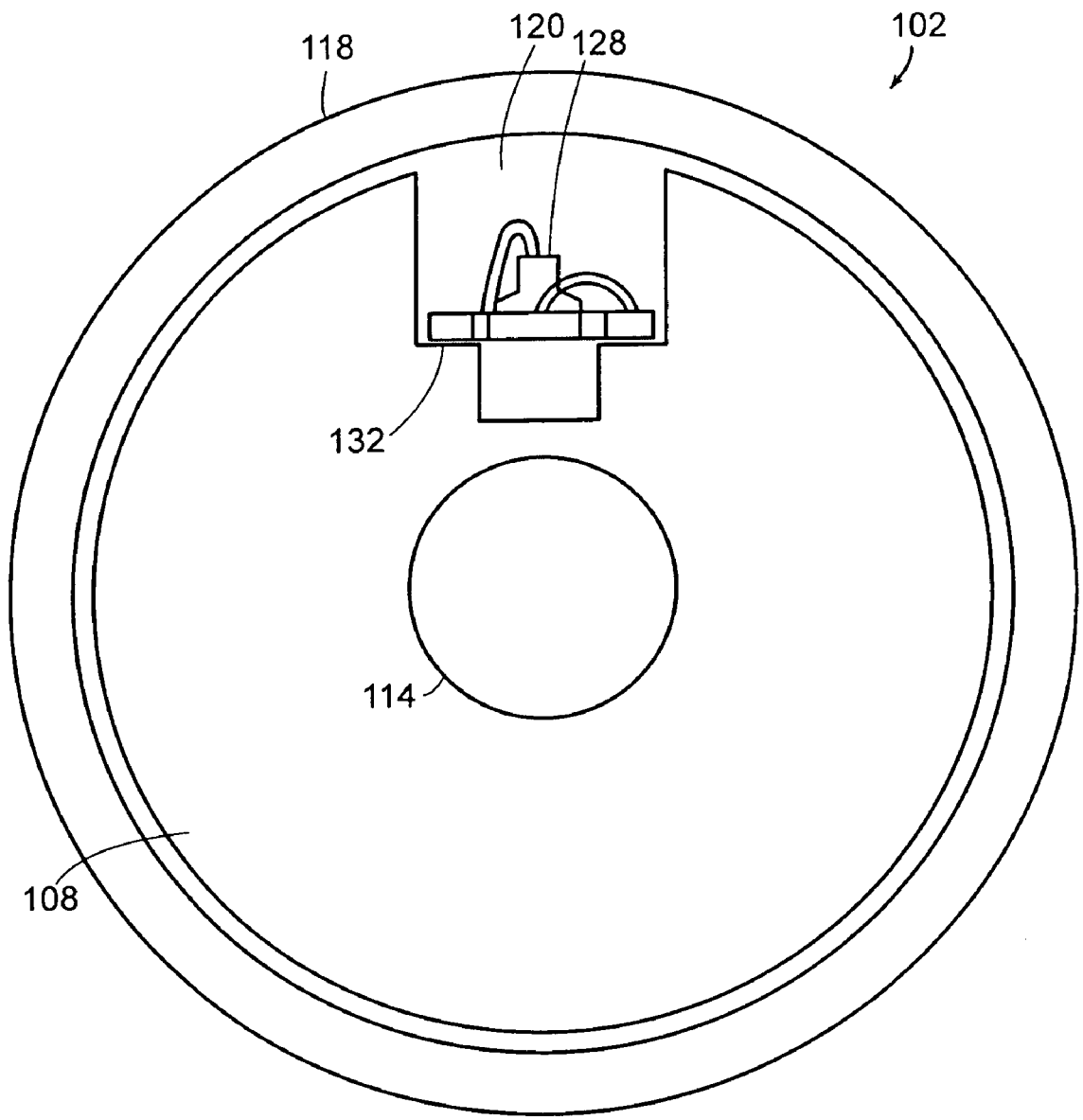
FIG. 2 is a distal end view cross section of light probe shown in FIG. 1.

FIG. 2 is a distal end view of the probe 102 of FIG. 1. In FIG. 2, the bore 114 is shown substantially centered in the shaft 108. The plurality of light-emitting devices 128 is maintained substantially centered in the passage 120 by retention on a mounting member 132, thereby providing immersion of the plurality of light-emitting devices 128 in the coolant flowing through the passage 120. The probe 102 is shown to be substantially cylindrical in cross section, but probes of the present invention may have any convenient cross section. For example, a probe of the present invention may have an oval or a polygonal cross section.

Figure 3:
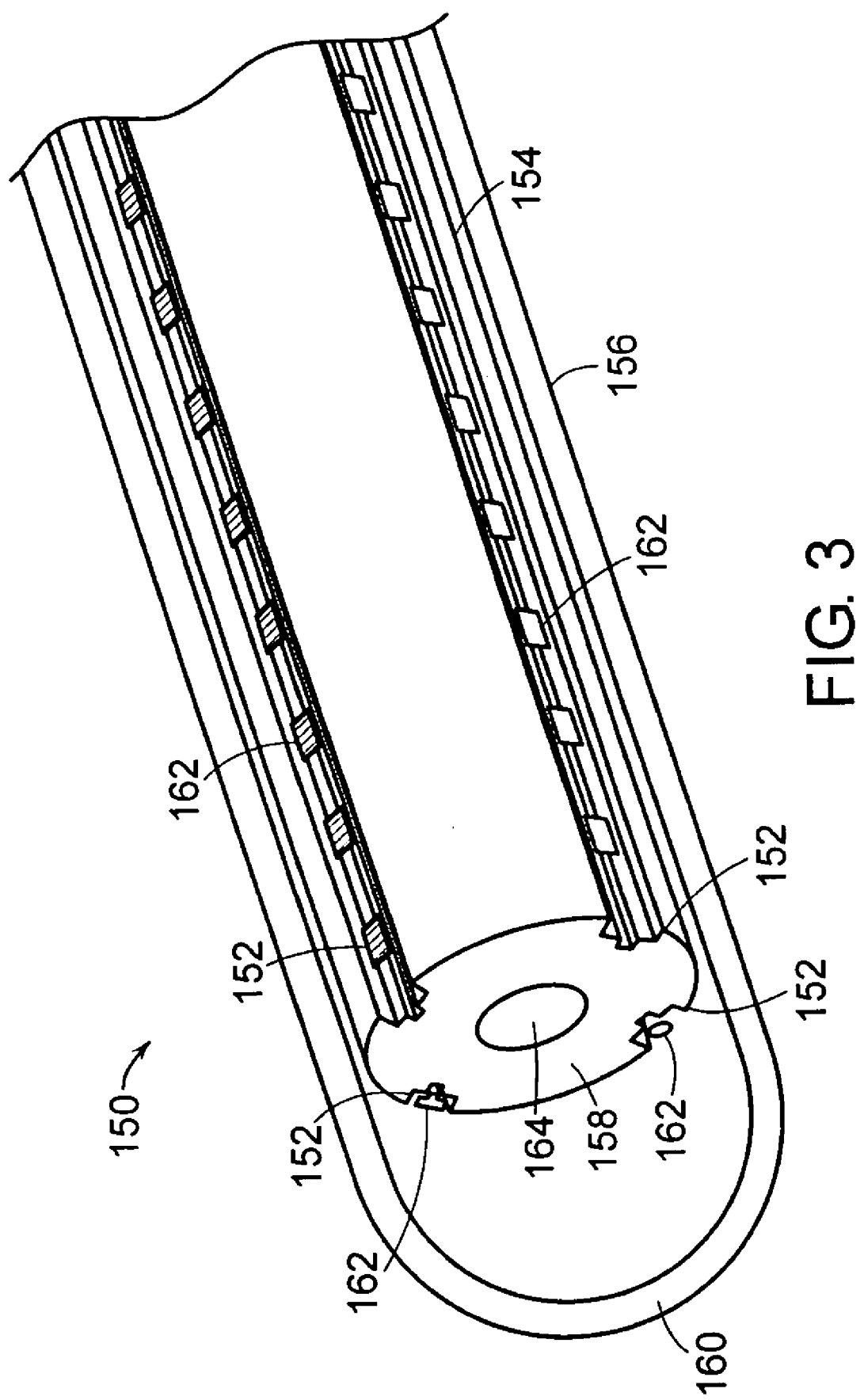
FIG. 3 is a perspective view of a light probe of the present invention having four passages for light-emitting devices.

FIG. 3 shows a distal end section of another exemplary embodiment of a probe 150 of the present invention. The probe 150 is similar in structure to the embodiment of the probe 102 illustrated in FIGS. 1 and 2, but the probe 150 includes four passages 152 distributed circumferentially between a shaft 154 and a sheath 156. The shaft 154 has a distal shaft end 158 and the sheath 156 has a distal sheath end 160 that is closed.

A plurality of light-emitting devices 162 is disposed in each of the four passages 152. The shaft 154 includes a longitudinal bore 164 that is in fluid communication with each of the four passages 152. The probe 150 may be configured for coolant to flow distally through the bore 164 and proximally through each of the four passages 152. The probe 150 may alternatively be configured for coolant to flow distally through each of the four passages 152 and proximally through the bore 164. The four passages 152 and the bore 164 are preferably dimensioned so as to provide a substantially equal distribution of coolant flow among the four passages.

Figure 4:
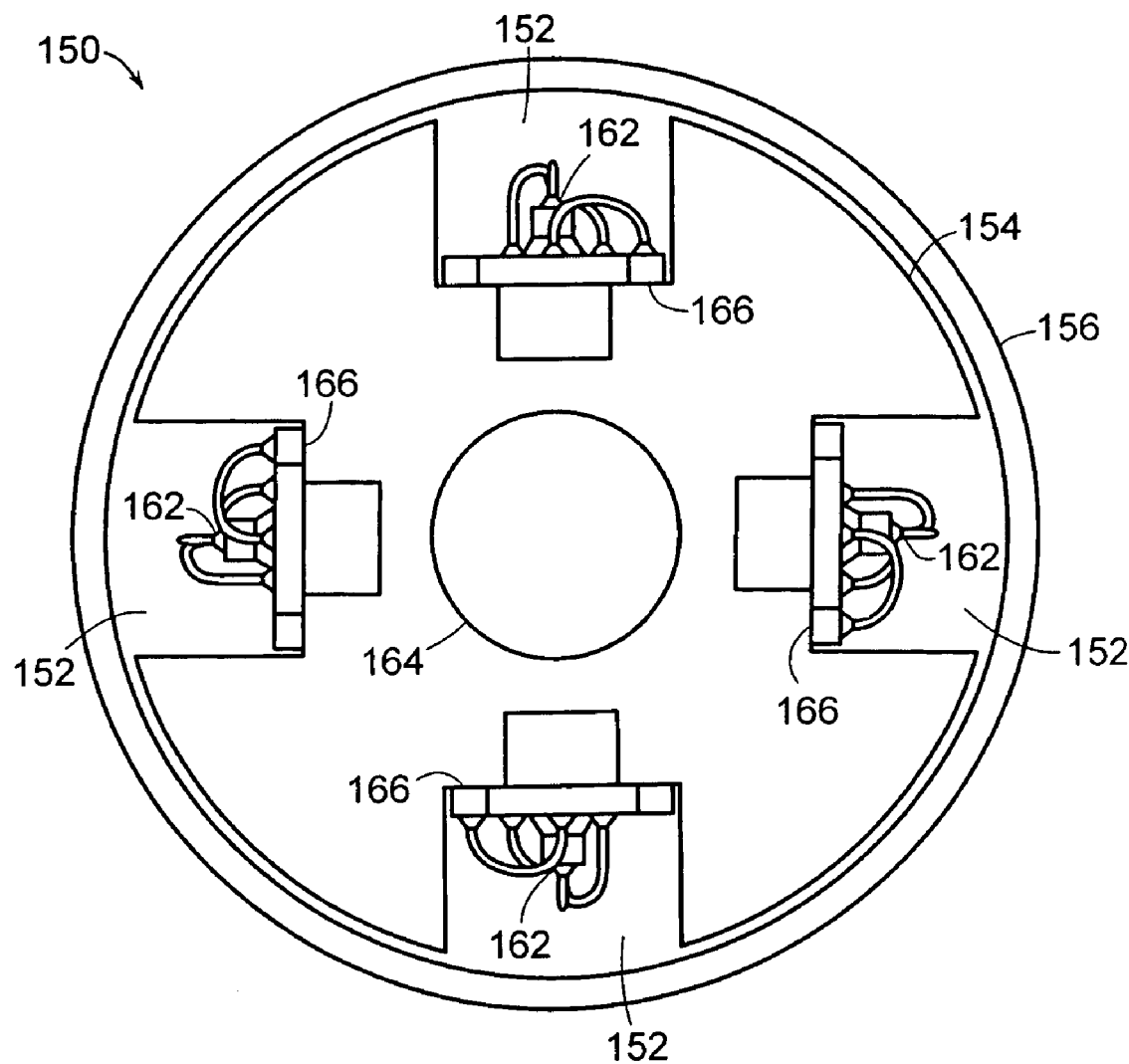
FIG. 4 is a distal end view cross section of the light probe shown in FIG. 3.

FIG. 4 is a distal end view of the probe shown in FIG. 3. The plurality of light-emitting devices 162 in each of the four passages 152 is preferably maintained substantially centered in the each of the four passages 152 by retention on a mounting member 166, thereby providing immersion of the plurality of light-emitting devices 162 in the coolant. A probe of the present invention may include any number of passages and corresponding pluralities of light-emitting devices disposed therein. In an embodiment, a probe of the present invention includes a plurality of light-emitting devices disposed in each of six passages circumferentially distributed around a shaft.

Figure 5:
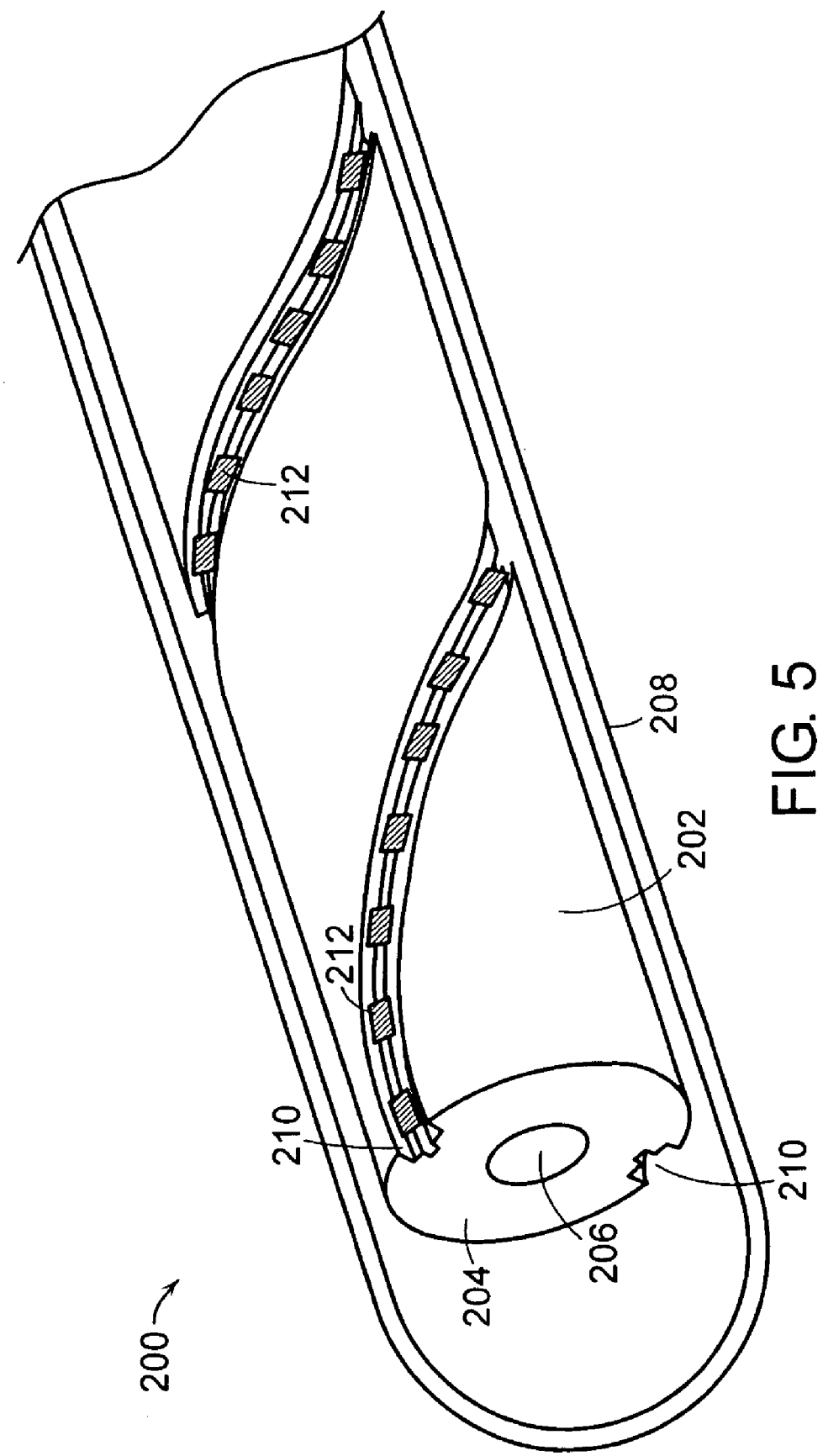
FIG. 5 is a perspective view of a light probe of the present invention having helical passages for light-emitting devices.

FIG. 5 illustrates an embodiment of a distal end section of another probe 200 of the present invention. The probe 200 includes a shaft 202 having a distal shaft end 204 and a longitudinal bore 206. The probe also includes a sheath 208 and at least one helical passage 210 defined between the sheath 208 and the shaft 202 for receiving a plurality of light-emitting devices 212. The probe 200 is illustrated with two helical passages, but a probe of the present invention may include any number of helical passages, each with a corresponding plurality of light-emitting devices. Other than including helical rather than longitudinal passages, the probe 200 may be of similar construction to the other embodiments of probes described previously.

Figure 6:
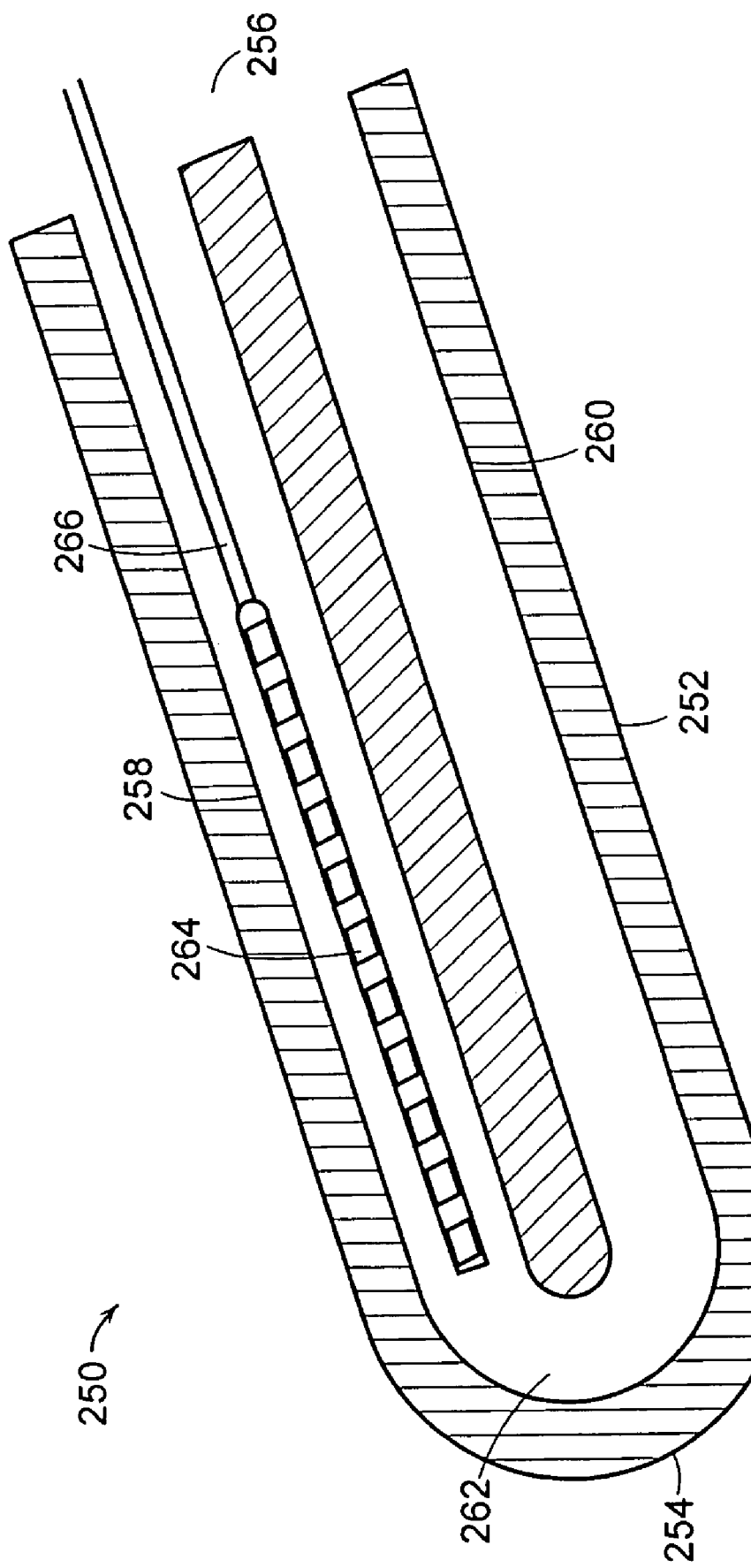
FIG. 6 is a cross sectional view of another light probe of the present invention.

FIG. 6 illustrates a distal section of another embodiment of a light-emitting probe 250 of the present invention. The probe 250 includes a flexible tube 252 preferably polymeric having a distal end 254 and a proximal end 256. The tube 252 has a first longitudinal internal channel or passage 258 in fluid communication with the proximal end 226. The tube 252 also has a second longitudinal internal passage 260 substantially parallel to the first passage 258. The second passage is in fluid communication with the proximal end 256. The first passage 258 is in fluid communication with the second passage 260 at a junction 262 within the tube 252. The first passage 258 and the second passage 260 are adapted at the proximal end 256 for coupling to an external coolant source for flowing a coolant through the first 258 and second passage 260.

One or more light-emitting device 264 is disposed in one or both of the first internal passage 258 and the second internal passage 260. A plurality of electrical leads 266 electrically connects the one or more light-emitting device 264 through the proximal end 256 to an external electric power source for energizing the one or more light-emitting device. The one or more light-emitting device 264 may be one or more light-emitting diode. In an embodiment the one or more light-emitting device 264 is a plurality of light-emitting diodes in a spaced-apart longitudinal array along at least one of the first internal passage 258 and the second internal passage 260. The tube is at least partially transmissive of light emitted by the one or more light-emitting device 264 either in whole or at locations proximate to the one or more light-emitting device 264. In an embodiment, the tube is biocompatible.

Liquid-cooled probes of the present invention can be constructed to produce high light output power in small diameter packages. For example, one light-emitting probe of the present invention 5 mm in diameter and having four passages for arrays of light-emitting diodes longitudinally spaced one millimeter apart and operating in a wavelength band near 405 nm has an approximate output power substantially equal to or greater than one watt per centimeter of probe length. In an embodiment, a light-emitting probe of the present invention having a radius of substantially 5 millimeters produces light having an optical power of approximately five watts per centimeter of probe length.

A plurality of light-emitting devices for inclusion in a flexible, light-emitting probe of the present invention can be configured as a unitary longitudinal array of light-emitting devices for assembly into the probe, or can be configured in segments. FIGS. 7 through 13 and the discussions thereof illustrate examples of unitary light-emitting arrays for use in conjunction with the probes illustrated in FIGS. 1 through 6 and the discussions thereof, as well as with other probes.

Figure 7:
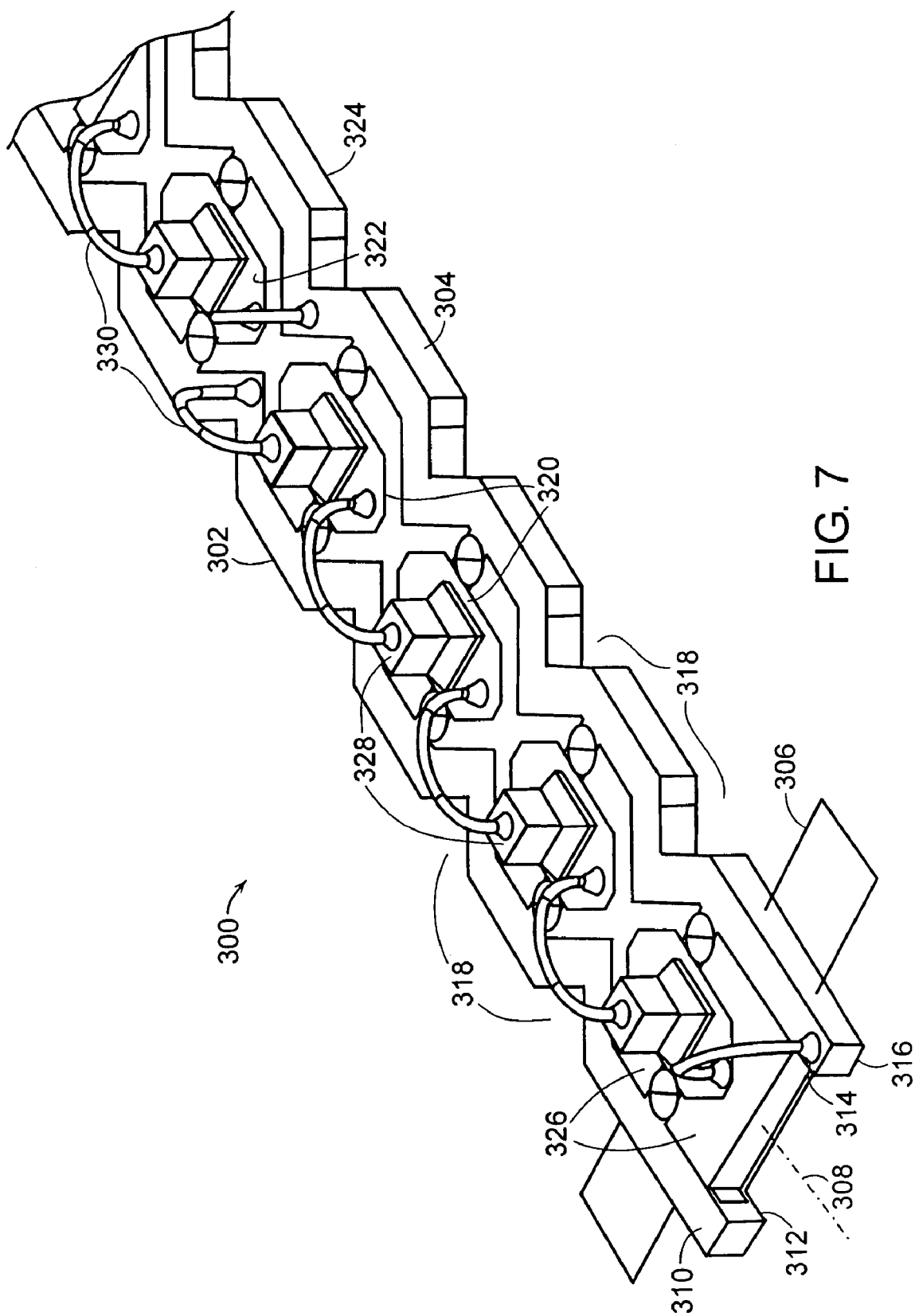
FIG. 7 is a perspective view of a flexible light-emitting diode array of the present invention.

FIG. 7 shows an embodiment of a portion of an elongate light-emitting diode array 300 of the present invention. The array 300 includes a first flexible, electrically conductive buss 302 and a second flexible, electrically conductive buss 304 disposed opposite the first buss 302. By disposed opposite we mean that the first buss 302 and the second buss 304 are positioned substantially parallel, but are not in electrical contact with one another. The first buss 302 and the second buss 304 define a plane 306 and an axis 308 in the plane. The first buss 302 has a first buss top surface 310 defined here as being above the plane 306 and a first buss bottom surface 312 below the plane 306. The second buss has a second buss top surface 314 above the plane 306 and a second buss bottom surface 316 below the plane 306. Each of the first buss 302 and the second buss 304 includes a plurality of longitudinally spaced-apart convolutions 318. Although the first buss 302 and the second buss 304 are described as being positioned substantially parallel to each other, in an alternative embodiment the first buss 302 and the second buss 304 may be substantially coplanar, while not being substantially parallel or in electrical contact to each other. In another embodiment, first buss 302 and the second buss 304 may be in relative close proximity to each other, while not being substantially parallel, coplanar or in electrical contact to each other.

A plurality of electrically conductive platforms or islands 320 are spaced apart along the axis 308 between the first buss 302 and the second buss 304. Each of the plurality of islands has an island top surface 322 above the plane 306 and an island bottom surface 324 below the plane 306. In an embodiment, the first buss 302, the second buss 304 and the plurality of islands are fabricated from a single planar strip of a metal. In an embodiment, the metal is copper. Each of the plurality of islands 320 is preferably connected to the first buss 302 and the second buss 304 through at least one flexible hinge member 326. The at least one hinge member 326 may be discontinuous and may comprise a flexible curable adhesive.

One of a plurality of light-emitting diodes 328 is electrically and mechanically mounted to the island top surface of each of the plurality of islands 320. The plurality of light-emitting diodes 328 may be mounted using soldering, an electrically conductive epoxy, or any mounting means compatible with the materials and structure of the array 300. The plurality of light-emitting diodes 328 is mounted at an orientation to direct emitted light in a direction generally away from the plane 306. A plurality of flexible electrical leads 330 electrically interconnect the plurality of light-emitting diodes 328 in an electrical circuit between the first buss 302 and the second buss 304. In an embodiment the first buss 302 is electrically connected as a cathode and the second buss 304 is electrically connected as an anode.

Figure 8:
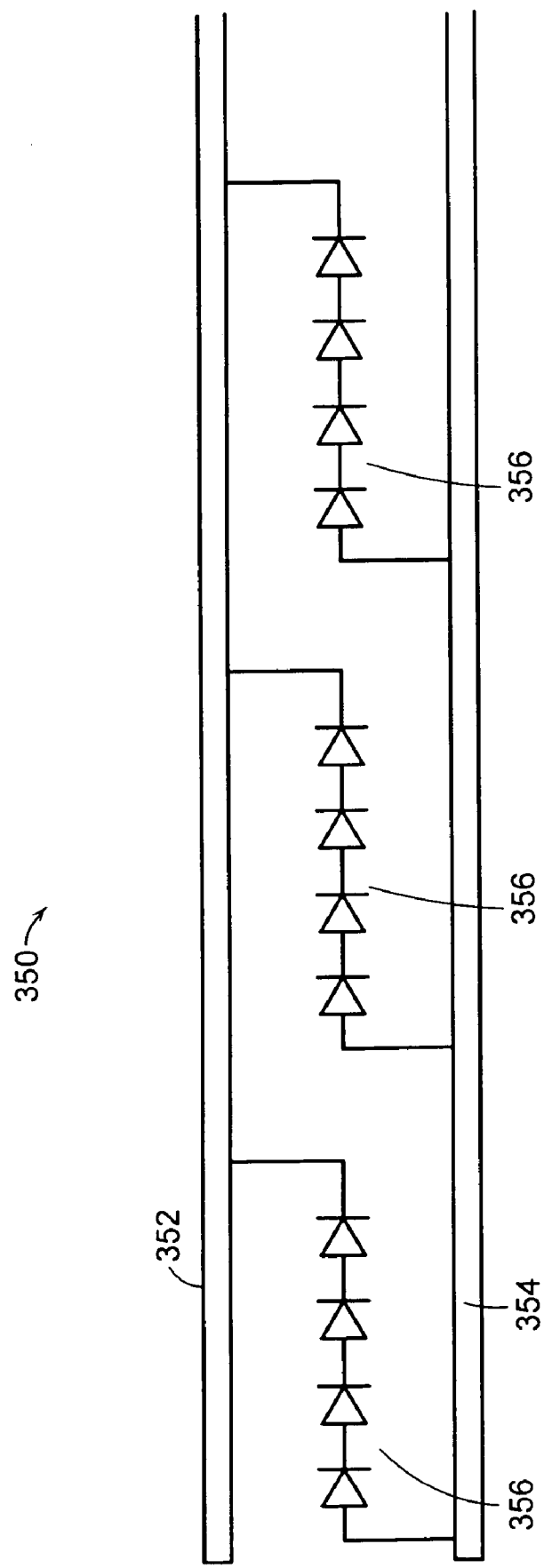
FIG. 8 is an electrical schematic of a series-parallel circuit showing parallel groups of four light-emitting diodes in series.

In an embodiment, the electrical circuit is a series-parallel circuit wherein groups of electrically series-connected light-emitting diodes of the plurality of light-emitting diodes 328, are electrically connected in parallel between the first buss 302 and the second buss 304. FIG. 8 shows schematically a series-parallel electrical circuit 350 between a cathode buss 352 and an anode buss 354. The circuit 352 includes groups of four light-emitting diodes 356 electrically connected in series, each of the groups 356 electrically connected in parallel between the cathode 352 and the anode 354. The number in each group of light-emitting diodes 356 in each group of light-emitting diodes 356 may be varied, and each group can include one or more light-emitting diodes 356. Each of the light-emitting diodes 356 in each group of light-emitting diodes 356 is considered to be electrically connected to the first buss 302 or the second buss 304 either directly or indirectly.

The array 300 of FIG. 7 is flexible about the axis 308. FIGS. 9A and 9B illustrate flexibility of the array 300 out of the plane 306. FIG. 9A illustrates a side view of the array 300 without flexion. For illustrative purposes, the plurality of flexible electrical leads 330, which flex easily with flexion of the array 300, are not shown in FIG. 9A or 9B. FIG. 9B illustrates a side view of the array 300 in flexion out of the plane 306. Flexion of the array 300 out of the plane 306 comprises flexion of the first buss 302, the second buss 304, and the at least one flexible hinge member 326 (not visible in FIGS. 9A and 9B).

FIGS. 10A and 10B illustrate flexibility of the array 300 in the plane 306. FIG. 10A illustrates the array 300 in plan view, without flexion. For illustrative purposes, the plurality of flexible electrical leads 330, which flex easily with flexion of the array 300, are not shown in FIG. 10A or 10B. FIG. 10B illustrates a plan view of the array 300 in flexion in the plane 306. Flexion of the array 300 in the plane 306 comprises extension or compression of the at least one the plurality convolutions 318 along at least one of the first buss 302 and the second buss 304, along with flexion, expansion or compression of the at least one flexible hinge member 326.

Figure 11:
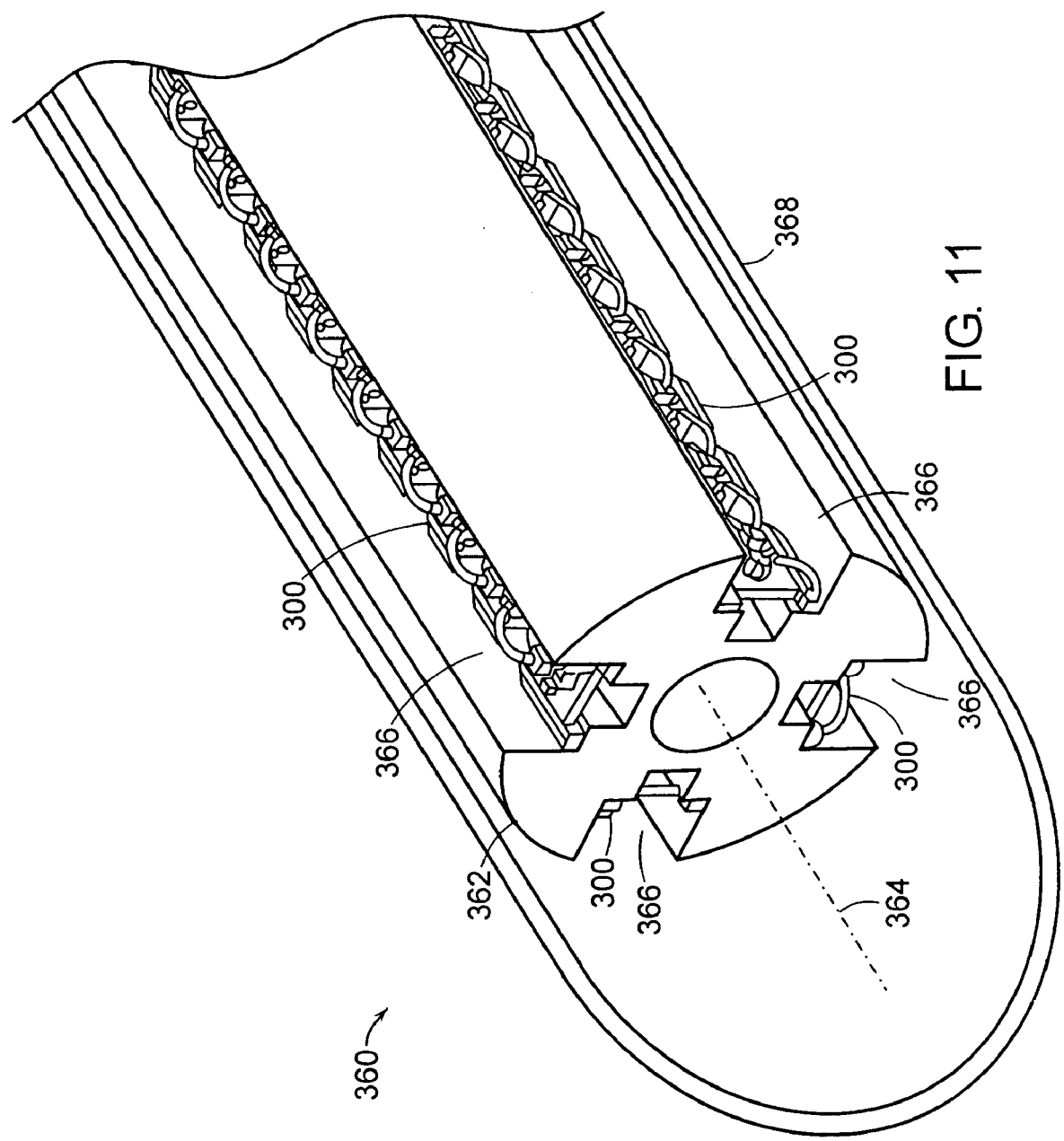
FIG. 11 is a perspective view of a light-emitting probe of the present invention incorporating the light-emitting array of FIG. 7.

FIG. 11 illustrates an embodiment of a flexible probe 360 of the present invention incorporating the light-emitting array 300. A flexible shaft 362 having a shaft axis 364 has four longitudinal grooves 366, each configured for mounting the light-emitting array 300. A sheath 368 closely surrounds the shaft 362. The in-plane and out-of-plane flexibility of each array 300 enables the flexible shaft 362 to be bent in any direction about the shaft axis 364 without damaging any of the arrays 300. Flexibility is improved through the structure of the light-emitting array 300, which can be referred to as an "open frame" structure.

Figure 12:
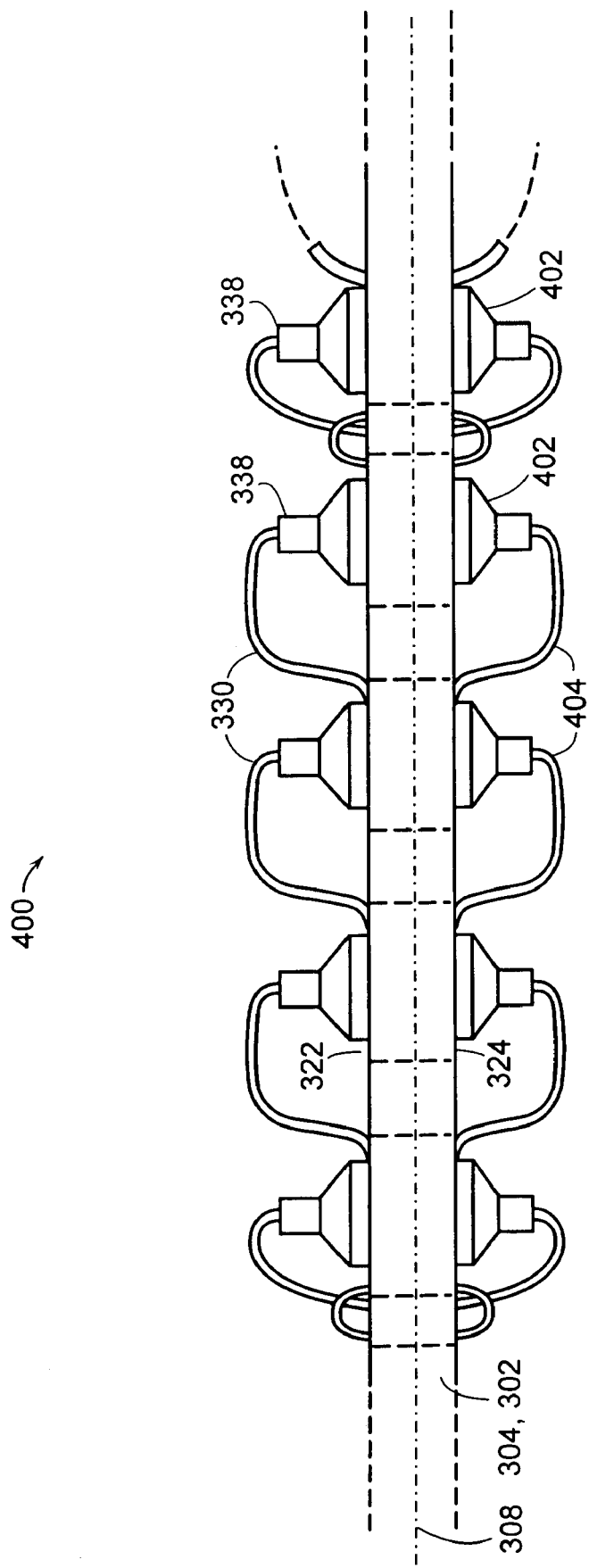
FIG. 12 is a side view of a two-sided light-emitting diode array of the present invention.

FIG. 12 shows a side view of an embodiment of a two-sided light-emitting array 400 of the present invention. The two-sided array 400 resembles the array 300 of FIG. 7 with the exception that the two-sided array 400 of FIG. 11 additionally may accommodate light-emitting diodes 402 mounted to the island bottom surface 324 of each of the plurality of islands 320. A corresponding plurality of flexible electrical leads 404 electrically interconnect the complementary plurality of light-emitting diodes 402 in an electrical circuit between the first buss 302 and the second buss 304. The two-sided array 400 emits light in directions both above and below the plane 306, and may accommodate a total of twice as many light-emitting diodes per unit length, as does the array 300 having only the plurality of light-emitting diodes.

Figure 13:
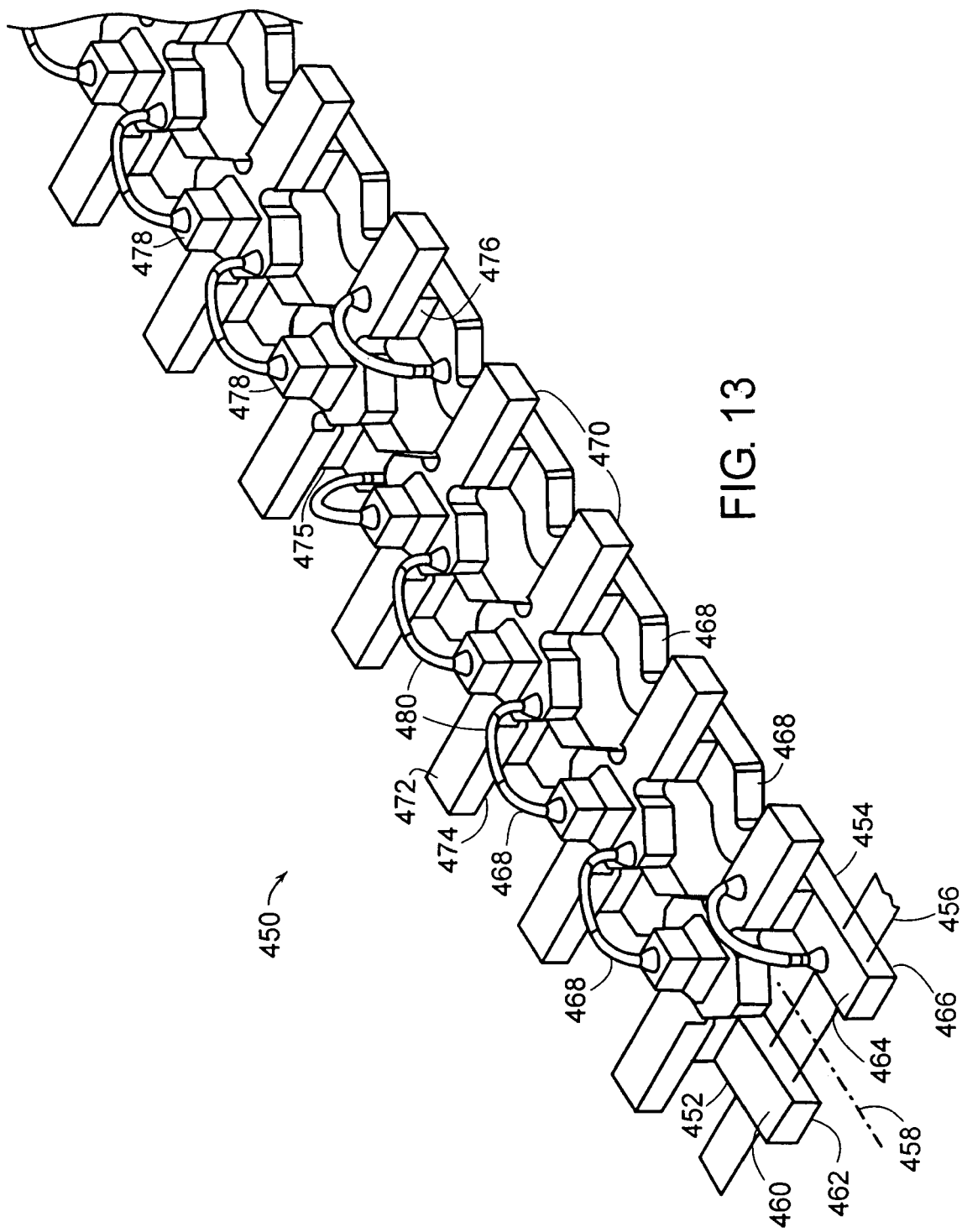
FIG. 13 is a perspective view of another flexible light-emitting diode array of the present invention having transverse positioning members.

FIG. 13 shows an embodiment of a portion of an elongate light-emitting diode array 450 of the present invention that has an electrical buss structure similar to the embodiment illustrated in FIG. 7, but wherein electrically conductive islands for mounting light-emitting diodes are positioned out of the plane defined by the busses, and include transverse positioning members. The array 450 includes a first flexible, electrically conductive buss 452 and a second flexible, electrically conductive buss 454 disposed opposite the first buss 452. The first buss 452 and the second buss 454 are substantially parallel to one another, defining a plane 456 and an axis 458 in the plane. The first buss 452 has a first buss top surface 460 defined here as being above the plane 456 and a first buss bottom surface 462 below the plane 456. The second buss 454 has a second buss top surface 464 above the plane 456 and a second buss bottom surface 466 below the plane 456. Each of the first buss 452 and the second buss 454 preferably includes a plurality of longitudinally spaced-apart convolutions 468. The plurality of convolutions 468 imparts flexibility of the array 450 in the plane 456. Flexibility of the first buss 452 and the second buss 454 impart flexibility of the array 450 out of the plane 456.

A plurality of electrically conductive islands 470 are preferably spaced apart along the axis 458 bridging the first buss 452 and the second buss 454. Each of the plurality of islands has an island top surface 472 and a island bottom surface 474. In an embodiment, the first buss 452, the second buss 454 and the plurality of islands 470 are all made of copper. The island bottom surface 474 of each of the plurality of islands 470 is connected to the first buss top surface 460 through a first hinge member 475 which is preferably flexible. The island bottom surface 474 of each of the plurality of islands 470 is connected to the second buss top surface 464 through a second hinge member 476 which is preferably flexible. Each of the first 475 and the second hinge member 476 may comprise a flexible curable adhesive.

One of a plurality of light-emitting diodes 478 is electrically and mechanically mounted to the island top surface of each of the plurality of islands 470. The plurality of light-emitting diodes 478 may be mounted using soldering, an electrically conductive epoxy, or any mounting means compatible with the materials and structure of the array 450. The plurality of light-emitting diodes 478 is mounted at an orientation to direct emitted light in a direction generally away from the plane 456. A plurality of flexible electrical leads 480 electrically interconnect the plurality of light-emitting diodes 478 in an electrical circuit between the first buss 452 and the second buss 454. In an embodiment the first buss 452 is electrically connected as a cathode and the second buss 454 is electrically connected as an anode. The plurality of islands 470 also position the array 450 when it is disposed in a passage of a light-emitting probe.

Figure 14:
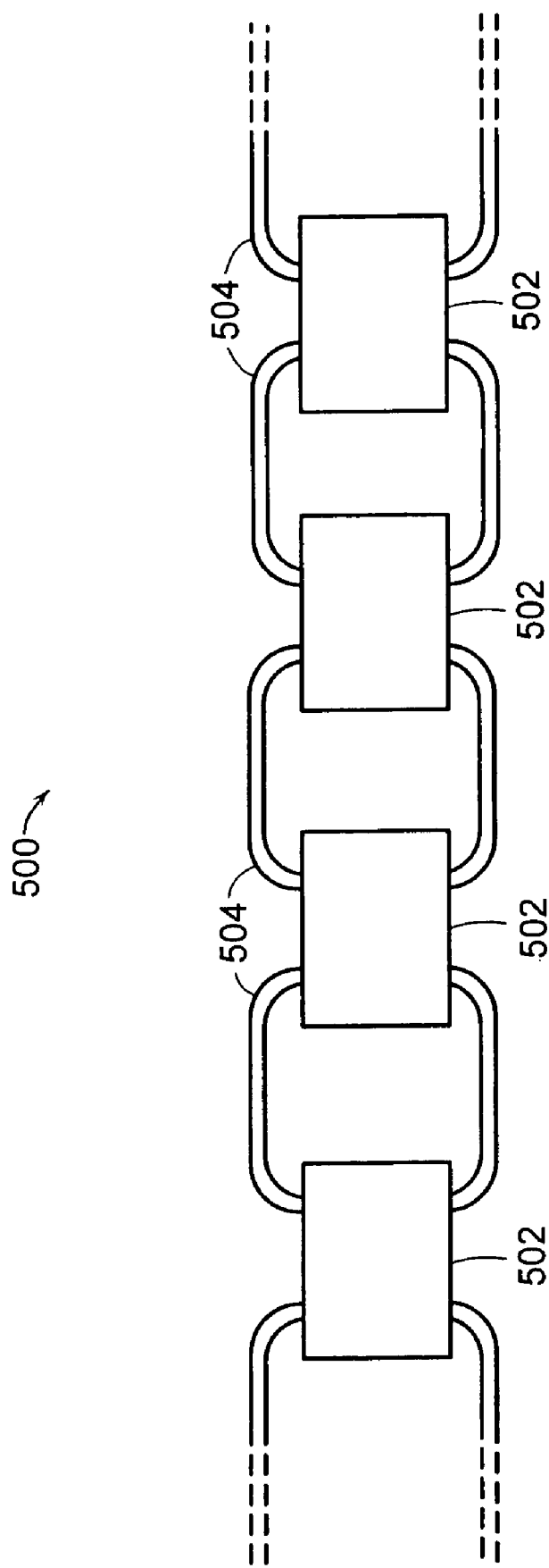
FIG. 14 shows a segmented light-emitting array of the present invention.
Figure 15:
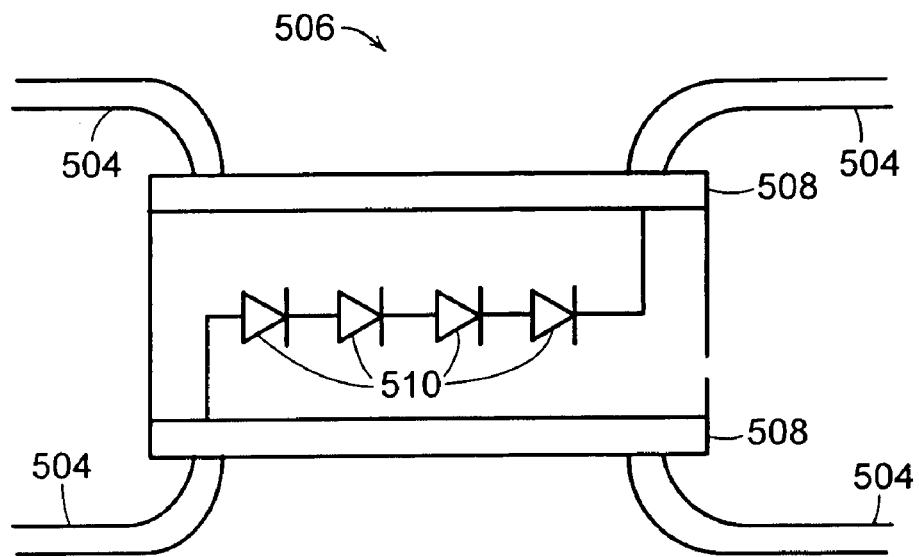
FIG. 15 shows an exemplary segment of the segmented array of FIG. 14.

FIG. 14 shows an embodiment of a section of a segmented light-emitting array 500 of the present invention. The segmented array 500 includes a plurality of light-emitting segments 502 structurally and electrically interconnected by a plurality of flexible electrical leads 504. The plurality of flexible electrical leads 504 interconnects the plurality of light-emitting segments 502 in electrical parallel. In an embodiment, the plurality of flexible electrical leads 504 comprises longitudinal convolutions along the segmented array. An exemplary segment 506 of the plurality of light-emitting segments 502 is shown schematically in FIG. 15. The exemplary segment 506 includes two electrical busses 508 that provide electrically parallel connections to the plurality of electrical leads 504. Four light-emitting diodes 510 are connected in electrical series between the busses 508 within the exemplary segment 506. The overall electrical circuit for this embodiment of the segmented array 500 is a series-parallel circuit as described herein in association with FIG. 8. The segmented light-emitting array 500 may include any number of light-emitting diodes within each segment of a plurality of segments 502. In another embodiment, each segment of the plurality segments 502 includes one light-emitting diode.

Figure 16:
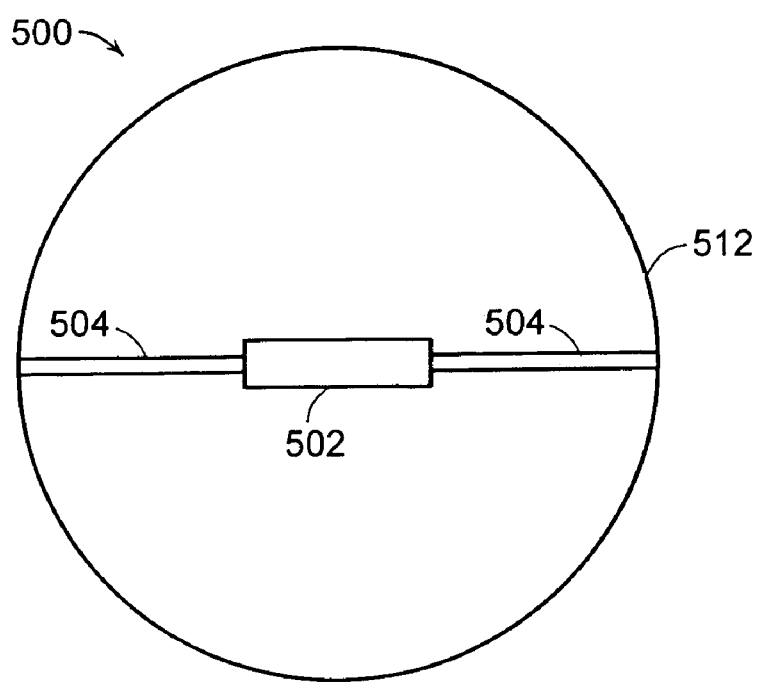
FIG. 16 is an end view of the segmented array of FIG. 14, centered in a cylindrical passage.

In another embodiment, the plurality of electrical leads 504 also serves as a plurality of positioning members to physically center the segmented array 500 within an internal passage of a light-emitting probe of the present invention. FIG. 16 is an end view of the segmented array 500 of FIG. 14. Each of the plurality of light-emitting segments 502 is substantially centered in a passage 512 by the plurality of flexible electrical leads 504. In an embodiment, the passage 512 has a circular cross section. In another embodiment, the passage 512 has a polygonal cross section having an even number of vertices for orienting the segmented array 500. In yet another embodiment, the passage 512 includes longitudinal features for registering the plurality of electrical leads 504, thereby orienting the segmented array 500 within the passage 512.

Figure 17:
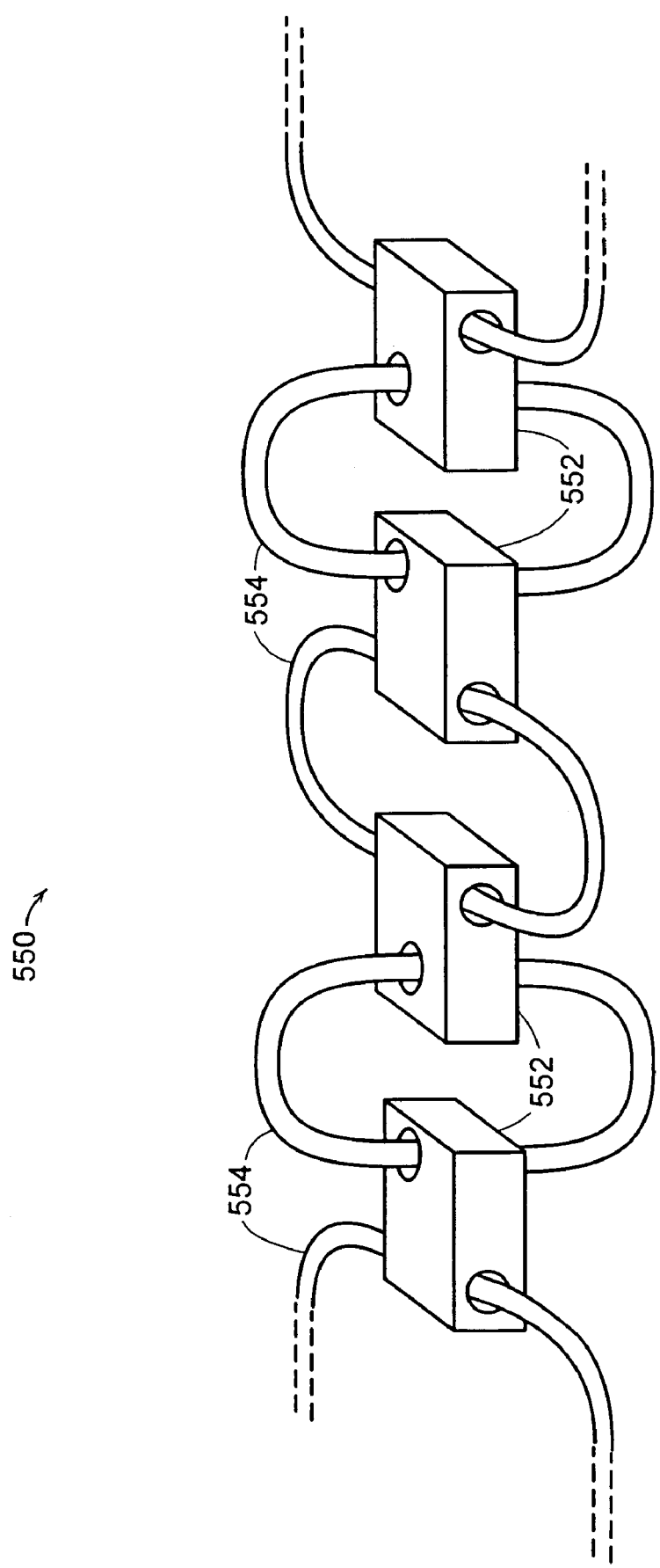
FIG. 17 shows an example of a three-dimensional lead structure of a segmented array of the present invention.
Figure 18:
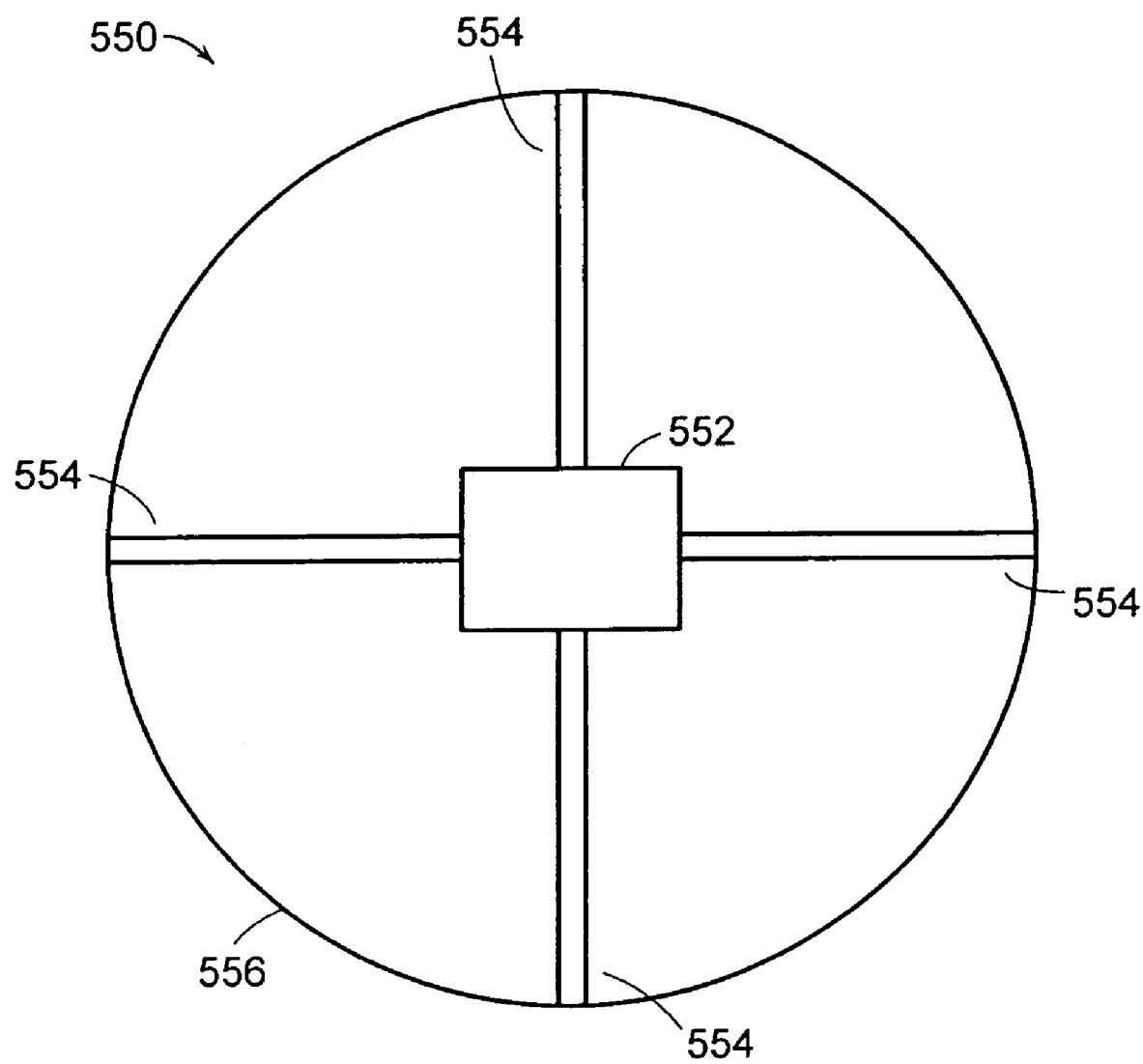
FIG. 18 is an end view of the segmented array of FIG. 17, centered in a cylindrical passage.

FIG. 17 shows an exemplary embodiment of a segmented light-emitting array 550 of the present invention including a plurality of light-emitting segments 552 interconnected by a plurality of flexible electrical leads 554 configured as a three-dimensional structure. FIG. 18 is an end view of the segmented array 550 of FIG. 17. Each of the plurality of light-emitting segments 552 is substantially centered in a passage 556 by the plurality of flexible electrical leads 554. In an embodiment, the passage 556 has a circular cross section. In another embodiment, the passage 556 has a polygonal cross section having an integral multiple of four vertices for orienting the segmented array 550. In yet another embodiment, the passage 512 includes longitudinal features for registering the plurality of electrical leads 504, thereby orienting the segmented array 500 within the passage 512.

Embodiments of segmented light-emitting arrays of the present invention may be physically flexible through flexion of the plurality of flexible electrical leads that interconnect light-emitting segments. The flexible electrical leads also may provide flexibility for a segmented light-emitting array by compression or extension of individual leads between adjacent light-emitting segments, in a manner similar to in-plane flexion of the plurality of convolutions 318 of the electrical busses 302, 304 shown in FIG. 10B.

Figure 19:
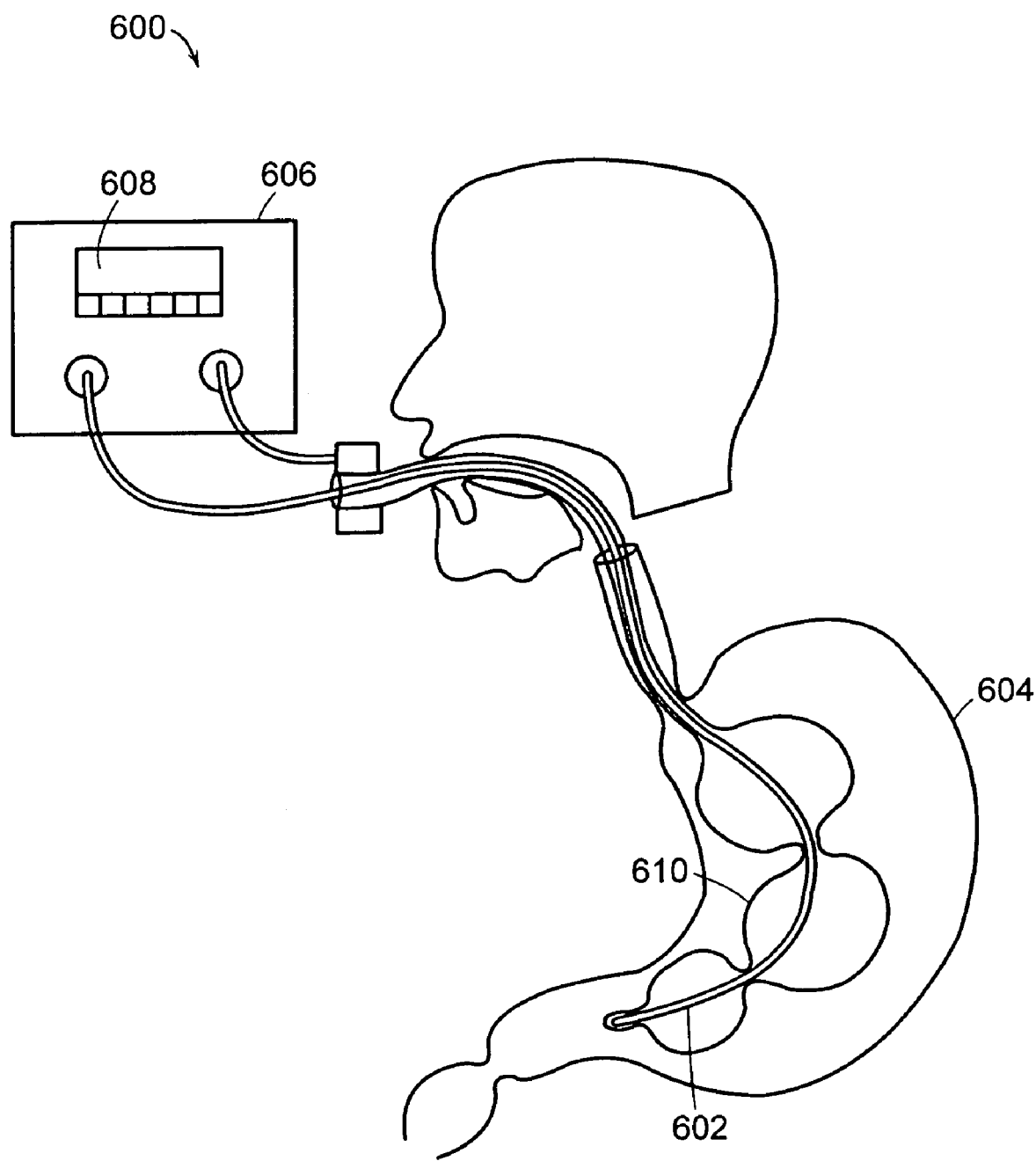
FIG. 19 shows a phototherapy system of the present invention, deployed in a human gastrointestinal tract.

FIG. 19 shows an embodiment of a phototherapy system 600 of the present invention. The phototherapy system 600 includes a light-emitting probe 602 for delivering light to the interior of a body lumen 604 (shown as a human stomach in FIG. 19). The phototherapy system 600 also includes a control unit 606 that provides electrical power and coolant for the probe 602. The control unit 606 also includes a user interface 608 for controlling the probe 602. The phototherapy system 600 may also include a balloon catheter 610 for guiding the probe 602 into the body lumen. The balloon catheter maintains a minimum distance between the probe 602 and a wall of the lumen 604 to limit the maximum intensity of light from the probe 602 reaching a treatment site. The balloon catheter 610 may be a multi-balloon catheter. Both the catheter 610 and the probe 602 may be controlled (inflated, deflated) through the user interface 606, or the catheter 608 may be controlled through a separate interface (not shown in FIG. 19).

Figure 20:
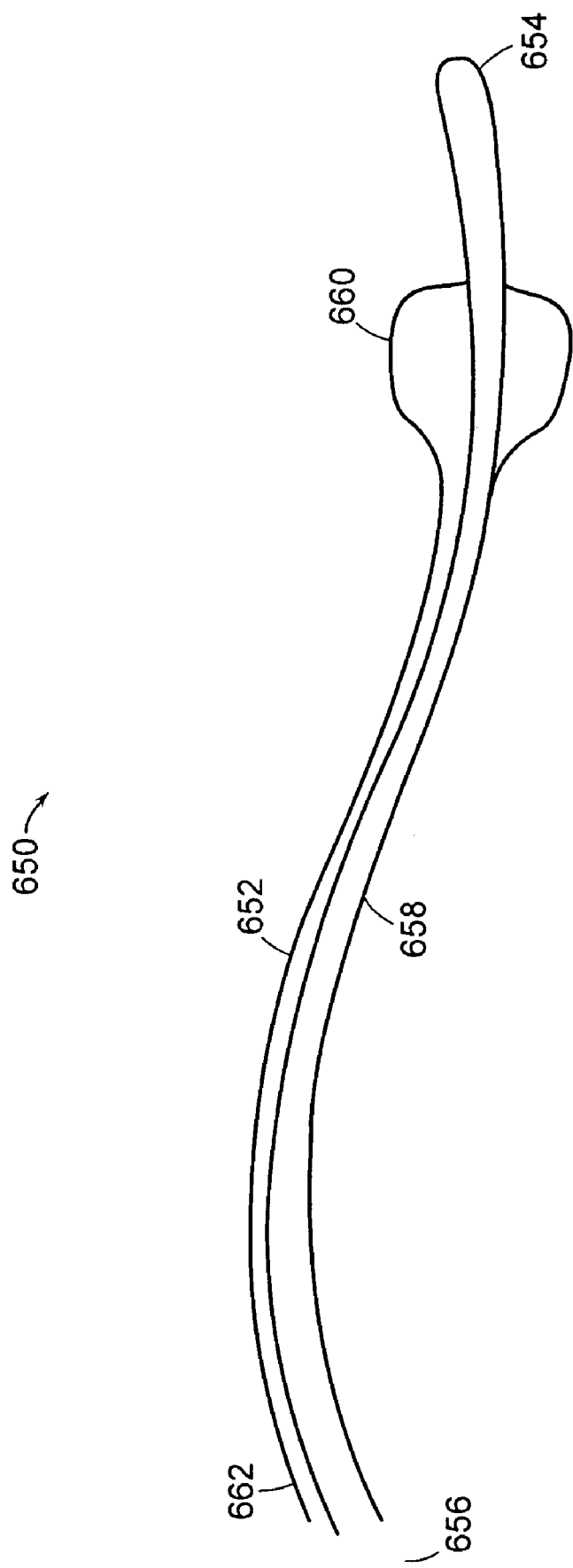
FIG. 20 shows a light-emitting probe 650 of the present invention including a positioning means.

An embodiment of a light-emitting probe of the present invention may include means to maintain a minimum distance from a wall of a lumen or for centering in a lumen. FIG. 20 illustrates an embodiment of a light-emitting probe 650 of the present invention including a positioning means. The probe 650 includes a probe body 652 having a distal end 654, a proximal end 656, a length therebetween and an outer surface 658 along the length. The outer surface 658 includes a reversibly inflatable member 660 surrounding the probe body 652 along at least a portion of the length. The inflatable member 660 is preferably circumferential and can be inflated or deflated through a longitudinal tube 662 adapted for connection at the proximal end 656 to an external inflation device providing a gaseous or a liquid working fluid. The longitudinal inflation tube 662 may be located external to the outer surface 658 or may be a longitudinal passage within the probe body 652. In an embodiment, the inflatable member inflates to a substantially predetermined working diameter. In another embodiment, the inflatable member is an elastic balloon.

The light-emitting probes and systems disclosed herein have many advantages, including but not limited to advantages related to liquid cooling. Liquid cooling of light-emitting diodes may enable these devices to output approximately four to ten times their nominal factory-specified light power without overheating. For example, an individual light-emitting diode having a manufacturer's specification of a maximum light power output of 12 milliwatts in air may be operated continuously at a light output power of approximately 120 milliwatts using liquid cooling. This increase in light output may enable a probe of the present invention to be used to treat a dramatically larger surface in a lumen, or to similarly decrease a treatment time, relative to known probes that are either uncooled, passively cooled, or air-cooled. Liquid cooling of light-emitting probes that incorporate these energy-consuming, active devices also may dramatically enhance patient safety over what can be achieved using other cooling means.

An exemplary embodiment of a medical procedure performed according to the present invention is the treatment of *H. Pylori* infection of the human stomach. Steps in an *H. Pylori* treatment procedure may include setting up a light-emitting probe for use. Setting up the probe may include attachment to a power source and a coolant source, calibration of the probe's light emission, and evaluation of the probe's condition and history to ensure patient safety and efficacy of the procedure.

In an embodiment, the physician inserts an endoscope into the patient's stomach and performs a diagnostic endoscopy. A guidewire may be placed in a biopsy channel of the endoscope and into the stomach, and the endoscope may be removed, leaving the guidewire in place. The light-emitting probe, placed in a catheter that may be a balloon catheter, is introduced into the stomach over the guidewire, which may then be removed, leaving the probe and the catheter in place in the stomach. One or more balloon of the catheter may be inflated, positioning the probe in the stomach, and the probe may be turned on to deliver a therapeutic dose of light to the stomach wall. The dose may be a predetermined, timed dose, or the dose may be measured and controlled during the light exposure using feedback from one or more sensor that may be incorporated into the probe.

Following delivery of the therapeutic light, the one or more balloon is deflated and the probe is withdrawn from the stomach. The probe may then cleaned and disinfected, for example, using glutaraldehyde, in preparation for use in another procedure. In an embodiment, the probe includes a mechanism or electronics to determine its remaining useful functional life.

Embodiments of light-emitting probes disclosed herein can be advantageous for many applications of light-emitting probes requiring light output, and particularly for applications requiring light to accelerate specific chemical reactions without causing thermal damage. Examples of non-medical applications of light probes disclosed herein in lumens include internal disinfection of pipes and ventilation ducts, rapid curing of internal coatings such as epoxy repairs of pipes, chemical cross-linking of polymeric surfaces to reduce susceptibility to chemical damage or wear, and photochemical deposition of optical or electronic materials within confined spaces. A probe to be used in a specific application may be designed to include light-emitting elements that emit light in a predetermined wavelength band for accelerating specific target chemical reactions for the application. For example, near ultraviolet light is used in the automotive industry and in and other industries to cure paint rapidly without thermal damage to the paint or an underlying part.

The enhanced physical flexibility of embodiments of light-emitting diode arrays disclosed herein may also be advantageous. In an embodiment, the structure of the arrays enables the arrays to be flexed in any direction about a longitudinal array axis. Known flexible arrays of light-emitting diodes are built on substrates that restrict flexibility in the substrate plane. Flexibility can be especially important, for example, in high-output probes that include circumferentially-distributed arrays of light-emitting diodes, where the arrays are oriented at a range of angles about their respective axes within the probe. In an embodiment, the structure of arrays also facilitates contact between the light-emitting diodes and a coolant in a liquid-cooled probe, for optimal heat transfer. Embodiments of arrays disclosed herein can be applied advantageously not only to liquid-cooled probes, but to any type of radiation-emitting probe, or probes utilizing other electrical devices.

Many changes in the details, materials, and arrangement of parts, herein described and illustrated, can be made by those skilled in the art. Although the invention has been shown and described with respect to detailed embodiments thereof, it will be understood that changes may be made without departing from the spirit and scope of the claimed invention. Accordingly, the following claims are not to be limited to the embodiments disclosed herein.

What is claimed is:

1. A flexible array, comprising:
(a) a first flexible conductive buss and a second flexible conductive buss, the first buss and the second buss being substantially parallel and not directly in contact with each other;
(b) a plurality of platforms disposed between the first buss and the second buss, each of the plurality of platforms being connected to the first buss by a first member and to the second buss by a second member; and
(c) at least one radiation emitting device disposed on at least one of the plurality of platforms, and electrically coupled to the first buss and the second buss;
wherein the first buss and the second buss each has a longitudinal axis, and at least one of the first buss and the second buss include a plurality of convolutions along its respective longitudinal axis.

2. The flexible array of claim 1, wherein:
(a) the first member is flexible and the second member is flexible;
(b) the first buss has a first buss side surface and the second buss has a second buss side surface, and each of the plurality of platforms has a first platform side surface and a second platform side surface; and
(c) each first member is disposed between the first buss side surface and a first platform side surface, and each second member is disposed between the second buss side surface and a second platform side surface.

3. The flexible array of claim 2, wherein each of the first and the second buss including the plurality of convolutions along its respective longitudinal axis.

4. The flexible array of claim 2, wherein the radiation emitting device is a light emitting diode.

5. The flexible array of claim 2, wherein the at least one radiation emitting device emits radiation substantially within a band of wavelengths adapted to treat diseased tissue.

6. The flexible array of claim 1, wherein:
(a) the first member is flexible and the second member is flexible;
(b) the first buss has a first top surface and the second buss has a second top surface, and each of the platforms has a top surface and a bottom surface; and
(c) each first member is disposed between the first top surface and a bottom surface, and each second member is disposed between the second top surface and a bottom surface.

7. The flexible array of claim 6, wherein each of the first and the second buss including at least one convolution along its respective longitudinal axis.

8. The flexible array of claim 6, wherein the at least one radiation emitting device comprises at least two radiation emitting devices, one disposed on a top surface the other disposed on a bottom surface.

9. The flexible array of claim 8, wherein the at least one radiation emitting device comprises a plurality of radiation emitting devices, and the plurality of radiation emitting devices are electrically coupled to the first buss and the second buss by a plurality of flexible electrical leads.

10. The flexible array of claim 9, wherein the plurality of flexible electrical leads electrically couple the plurality of radiation emitting devices between the first buss and the second buss in a series-parallel circuit.

11. The flexible array of claim 10, wherein the series-parallel circuit comprises a plurality of groups of at least four radiation emitting devices in series, the plurality of groups being electrically in parallel.

12. The flexible array of claim 6, wherein the radiation emitting device is a light emitting diode.

13. The flexible array of claim 6, wherein the at least one radiation emitting device emits radiation substantially within a band of wavelengths adapted to treat diseased tissue.

14. The flexible array of claim 1, wherein each of the first and the second buss including the plurality of convolutions along its respective longitudinal axis.

15. The flexible array of claim 1, wherein the first buss and the second buss both are substantially in the same plane, and the first buss and the second buss each include the plurality of convolutions substantially in such plane.

16. The flexible array of claim 1, wherein the at least one radiation emitting device is a light emitting diode.

17. The flexible array of claim 1, wherein the at least one radiation emitting device emits radiation substantially within a band of wavelengths adapted to treat diseased tissue.

18. The flexible array of claim 17, wherein the band of wavelengths is substantially centered between approximately 400 nanometers and 410 nanometers.

19. The flexible array of claim 1, wherein the at least one radiation emitting device emits radiation substantially within a band of wavelengths adapted to modify the rate of a chemical reaction.

20. A flexible array, comprising:
(a) a plurality of segments, each segment having:
   (i) a first flexible conductive buss and a second flexible conductive buss, the first buss and the second buss being substantially parallel and not directly in contact with each other;
   (ii) a plurality of platforms disposed between the first buss and the second buss, the platforms being connected to the first buss by a first member and to the second buss by a second member; and
   (iii) at least one electrical device disposed on at least one platform, and electrically connected to the first buss and the second buss;
(b) a plurality of flexible electrical connectors, at least one electrical connector being disposed between the first flexible buss of one segment and the first flexible buss of a second segment, and at least one electrical connector being disposed between the second flexible buss of one segment and the second flexible buss of a second segment;
wherein the first member is flexible and the second member is flexible.

21. The flexible array of claim 20, wherein said plurality of flexible electrical connectors are adapted to position the segments within an elongated probe.

22. The flexible array of claim 20, wherein said plurality of flexible connectors are adapted to provide positioning in more than one geometrical plane.

23. The flexible array of claim 20, wherein the electrical devices are light-emitting diodes.

24. The flexible array of claim 20, wherein the first buss and the second buss each has a longitudinal axis, each of the first and the second buss including a plurality of convolutions along its respective longitudinal axis.

25. The flexible array of claim 20, wherein the at least one electrical device emits radiation substantially within a band of wavelengths adapted to treat diseased tissue.

26. An apparatus for delivering radiation, comprising:
(a) at least one longitudinal array comprising:
   (i) a first flexible conductive buss and a second flexible conductive buss, the first buss and the second buss being substantially parallel and not directly in contact with each other, the first buss and the second buss each including a plurality of convolutions;
   (ii) a plurality of platforms disposed between the first buss and the second buss, the platforms being connected to the first buss by a first member and to the second buss by a second member; and
   (iii) a plurality of radiation emitting devices, each disposed on at least one platform, and electrically coupled to the first buss and the second buss; and
(b) a flexible shaft, the flexible shaft having a distal end and a proximal end, and an outer surface defining at least one groove extending from a location near the distal end to the proximal end; and
(c) a flexible sheath proximate the shaft, the sheath and the at least one groove defining at least one channel, the at least one array disposed in the at least one channel.

* * * * *